United States Patent
Parthasarathy et al.

(10) Patent No.: US 12,417,823 B1
(45) Date of Patent: Sep. 16, 2025

(54) MULTI-REGIONAL INTELLIGENT CLASSIFICATION AND ROUTING

(71) Applicant: Kaiser Foundation Hospitals, Oakland, CA (US)

(72) Inventors: Subha Parthasarathy, Danville, CA (US); Narayanan Gopala, San Diego, CA (US); Pratabkumar Vemana, Marietta, GA (US); Raghunath Raman, San Jose, CA (US); Inna Fedoseyeva, Oakland, CA (US); Madhur Pande, Danville, CA (US); Sivasubramanian Sundaram, Oakland, CA (US)

(73) Assignee: Kaiser Foundation Hospitals, Oakland, CA (US)

( * ) Notice: Subject to any disclaimer, the term of this patent is extended or adjusted under 35 U.S.C. 154(b) by 183 days.

(21) Appl. No.: 18/331,847

(22) Filed: Jun. 8, 2023

Related U.S. Application Data

(60) Provisional application No. 63/350,669, filed on Jun. 9, 2022.

(51) Int. Cl.
*G16H 10/20* (2018.01)
*G06F 18/2415* (2023.01)

(52) U.S. Cl.
CPC ......... *G16H 10/20* (2018.01); *G06F 18/2415* (2023.01)

(58) Field of Classification Search
CPC ........ G16H 10/20; G16H 10/60; G16H 15/00; G16H 40/00; G16H 80/00; G06F 18/2415
See application file for complete search history.

(56) References Cited

U.S. PATENT DOCUMENTS

| | | | | |
|---|---|---|---|---|
| 2007/0124312 A1* | 5/2007 | Simpson | ................ | H04L 51/00 |
| 2012/0203569 A1* | 8/2012 | Altman | ................ | G16H 10/60 |
| | | | | 705/2 |
| 2014/0280453 A1* | 9/2014 | Mattison | ................ | H04L 51/52 |
| | | | | 709/202 |
| 2016/0182410 A1* | 6/2016 | Janakiraman | ........... | G06F 40/30 |
| | | | | 709/206 |
| 2019/0386917 A1* | 12/2019 | Malin | ..................... | H04L 69/08 |
| 2020/0065857 A1* | 2/2020 | Lagi | ................... | G06Q 30/0254 |

FOREIGN PATENT DOCUMENTS

| | | | | |
|---|---|---|---|---|
| WO | WO-2018065964 A1 * | 4/2018 | ........... | G06F 16/258 |
| WO | WO-2020205316 A1 * | 10/2020 | ......... | G06F 16/3329 |

OTHER PUBLICATIONS

Githinji et al.,Development of a text-messaging intervention to improve treatment adherence and post-treatment review of children with uncomplicated malaria in western Kenya, 2015, Malaria Journal, pp. 1-9. (Year: 2015).*

* cited by examiner

*Primary Examiner* — Christopher L Gilligan
(74) *Attorney, Agent, or Firm* — PATENT LAW WORKS LLP

(57) ABSTRACT

A system for multi-regional intelligent classification and routing based on processing a message uses an artificial intelligence platform. Artificial Intelligence (AI) and machine learning (ML) based approaches significantly optimize the user experience and efficiently utilize care coordination and delivery workflows in healthcare organizations. Trained machine learning models are used to intelligently route messages from a patient member seeking access to care, determining an intent and entities from the message to perform an action in response to their message.

20 Claims, 9 Drawing Sheets

MULTI-REGIONAL INTELLIGENT CLASSIFICATION AND ROUTING

CROSS-REFERENCE TO RELATED APPLICATIONS

The present application claims priority, under 35 U.S.C. § 119, of U.S. Provisional Patent Application No. 63/350,669, filed Jun. 9, 2022, and entitled "Multi-Regional Intelligent Classification And Routing," which is incorporated by reference in its entirety.

BACKGROUND

This specification generally relates to a system and method for processing messages to determine intent and priority. In particular, the specification relates to a system and method for intelligent message intent detection and routing. Still more particularly, the specification relates to a system and method for multi-regional intelligent classification and routing of messages.

Healthcare organizations, healthcare providers, physician offices, and hospitals continuously receive healthcare-related requests from users. Additionally, many users are beginning to interact with these entities via new technologies or channels such as via the web, video, online messaging, email, texting, in addition to the more traditional ways of interacting such as telephone or in-person conversations or appointments. Several issues arise with so many new and different ways of patient-entity interactions. The interactions are siloed without channel cross-over, limited options and lack of understanding, missed opportunities with human interactions, and an inability to seamlessly transition to another channel. Without channel integration and guidance, the users may have to exit and choose a new channel. Furthermore, the incoming messages are neither organized nor prioritized; and therefore, require a significant amount of human and other processing in order to identify the needs and respond in a timely manner.

This background description provided herein is for the purpose of generally presenting the context of the disclosure.

SUMMARY

The techniques introduced herein overcome the deficiencies and limitations of the prior art, at least in part, with a system and methods for providing intelligent message intent detection and routing. In one implementation, the system and method of the present disclosure identify the intents of incoming messages using advanced natural language processing (NLP) artificial intelligence (AI)/machine learning (ML) classification models, and based on the identified intents, perform defined pre-defined action(s). The system and method of the present disclosure may advantageously improve member/patient experience in real-time.

As messages are typed by members/patients, they are passed on to the platform through the gateway component that receives the message and either generates a new unique co-relation id or associates the message with an existing one if co-relation id already exists for the message. The gateway component then transforms the message to the common format and pushes it to an event queue (in Event Hub). The message is then picked up by Message Handler that combines all parts of the messages received so far and generates a directed acyclic graph (DAG) comprising of AI/ML classifier models required for identifying the intents and extracting related entities (such as, appointment date/time, location, provider). The DAG is executed by a classifier service that submits jobs for each classifier model in the DAG. The models return the intents and entities that are written to an event queue. The intent handler then picks up the intent payload from the event queue and then prepares payload to act on the pre-defined actions for each identified intent, and then passes on the payload to the transformation service and an action service via event queues. The transformation services convert the payload to the target service/API payload structure and action service invokes the target API/Service that fulfills the pre-defined action (for ex., invoke appropriate service to schedule the appointment). The action service receives the response from the target API/Service and passes it back to an action controller for logging/tracking purposes. The action controller again passes the status to gateway component for logging/tracking purposes.

A design time metadata store provides pre-configured information about each consumer and supported intents and actions.

The components of the intelligent message handling application individually keep track of the messages, the processing steps it has gone through, statuses and its final disposition. The operational metadata is spread across SQLDB tables and in log files stored in Data Lake/cloud storage.

The features and advantages described herein are not all-inclusive and many additional features and advantages will be apparent in view of the figures and description. Moreover, it should be understood that the language used in the present disclosure has been principally selected for readability and instructional purposes, and not to limit the scope of the subject matter disclosed herein.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

While the present disclosure may describe the techniques herein in the context of a patient member seeking healthcare services in hospitals, medical clinics and the like, it should be understood that the architecture, principles, and components of the present disclosure may also be used to provide intent determination, message routing, and automatic execution of actions in a variety of other contexts where messages are received and responsive to those messages particular actions need to be taken. For example, the present disclosure may be applied to retail sales, technical support services, insurance, and any other areas where intent determination and automatic messaging processing is important. The systems and methods described below may be applied to various other medical care, coordination, and delivery procedures in addition to those specifically set forth below.

Figure 1:
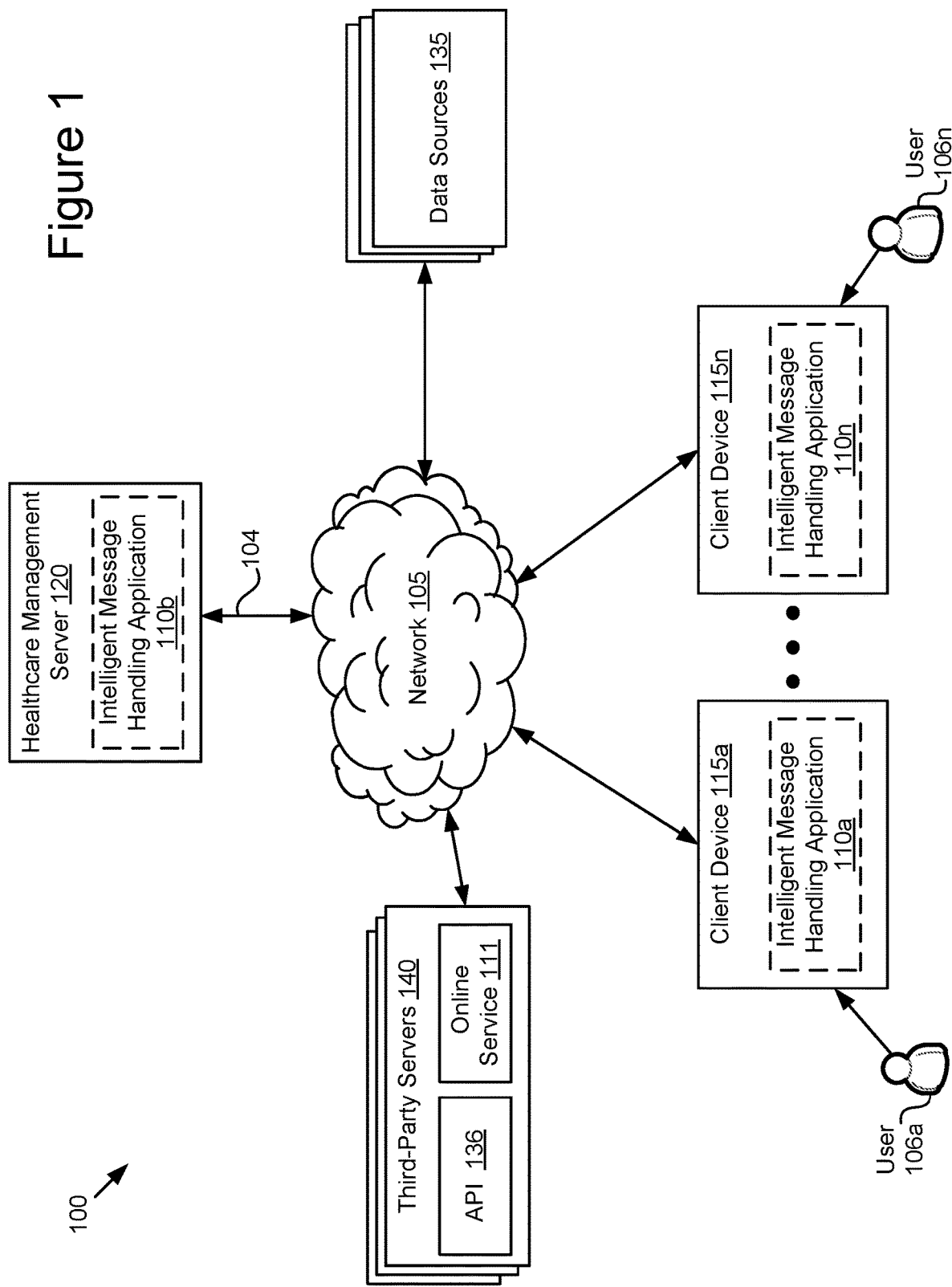
FIG. 1 is a high-level block diagram illustrating one example implementation of a system for intelligent message intent detection and routing.

FIG. 1 is a high-level block diagram illustrating one implementation of a system 100 for intelligent message intent detection, routing, and processing for delivering the appropriate healthcare services. The illustrated system 100 may include one or more client devices 115a . . . 115n that can be accessed by users, a healthcare management server 120, a plurality of data sources 135, and a plurality of third-party servers 140 which are communicatively coupled via a network 105 for interaction and electronic communication with one another. In FIG. 1 and the remaining figures, a letter after a reference number, e.g., "115a," represents a reference to the element having that particular reference number. A reference number in the text without a following letter, e.g., "115," represents a general reference to instances of the element bearing that reference number.

The network 105 may be a conventional type, wired or wireless, and may have numerous different configurations including a star configuration, token ring configuration, or other configurations. Furthermore, the network 105 may include any number of networks and/or network types. For example, the network 105 may include a local area network (LAN), a wide area network (WAN) (e.g., the Internet), virtual private networks (VPNs), mobile (cellular) networks, wireless wide area network (WWANs), WiMAX® networks, Bluetooth® communication networks, peer-to-peer networks, near field networks (e.g., NFC, etc.), and/or other interconnected data paths across which multiple devices may communicate, various combinations thereof, etc. The network 105 may also be coupled to or include portions of a telecommunications network for sending data in a variety of different communication protocols. In some implementations, the network 105 may include Bluetooth communication networks or a cellular communications network for sending and receiving data including via short messaging service (SMS), multimedia messaging service (MMS), hypertext transfer protocol (HTTP), direct data connection, WAP, email, etc. In some implementations, the data transmitted by the network 105 may include packetized data (e.g., Internet Protocol (IP) data packets) that is routed to designated computing devices coupled to the network 105. Although FIG. 1 illustrates one network 105 coupled to the client devices 115, the healthcare management server 120, the plurality of data sources 135, and the plurality of third-party servers 140, in practice one or more networks 105 can be connected to these entities.

The client devices 115a . . . 115n (also referred to individually and collectively as 115) may be computing devices having data processing and communication capabilities. In some implementations, a client device 115 may include a memory, a processor (e.g., virtual, physical, etc.), a power source, a network interface, software and/or hardware components, such as a display, graphics processing unit (GPU), wireless transceivers, keyboard, camera (e.g., webcam), sensors, firmware, operating systems, web browsers, applications, drivers, and various physical connection interfaces (e.g., USB, HDMI, etc.). The client devices 115a . . . 115n may couple to and communicate with one another and the other entities of the system 100 via the network 105 using a wireless and/or wired connection. Examples of client devices 115 may include, but are not limited to, laptops, desktops, tablets, mobile phones (e.g., smartphones, feature phones, etc.), server appliances, servers, virtual machines, smart TVs, media streaming devices, user wearable computing devices (e.g., fitness trackers, etc.) or any other electronic device capable of accessing a network 105. In the example of FIG. 1, the client device 115a is configured to implement an intelligent message handling application 110a described in more detail below. The client device 115 includes a display for viewing information provided by one or more entities coupled to the network 105. For example, the client device 115 may be adapted to send and receive data to and from the healthcare management server 120. While two or more client devices 115 are depicted in FIG. 1, the system 100 may include any number of client devices 115. In addition, the client devices 115a . . . 115n may be the same or different types of computing devices. The client devices 115a . . . 115n may be associated with the users 106a . . . 106n. For example, users 106a . . . 106n may include patient members, physicians, clinical staff, laboratory technicians, pharmacy technicians, administrative staff, call center agents, etc. of a health care organization. Each client device 115 may be associated with a data channel, such as a mobile application running on a user's smartphone, a computer in a doctor's office, a health tracking device, etc. These data channels may collect data related to one or more users and provide that data to the entities coupled to the network 105. In some implementations, the client devices 115 may be implemented as a computing device 200 as will be described below with reference to FIG. 2.

In the example of FIG. 1, the healthcare management server 120, the plurality of data sources 135, and the plurality of the third-party servers 140 may be, or may be implemented by, a computing device including a processor, a memory, applications, a database, and network communication capabilities similar to that described below with reference to FIG. 2.

In the example of FIG. 1, the healthcare management server 120 may be configured to implement an intelligent message handling application 110b. In some implementations, the healthcare management server 120 may be a hardware server, a software server, or a combination of software and hardware. For example, the healthcare management server 120 may include one or more hardware servers, virtual servers, server arrays, storage devices and/or systems, etc., and/or may be centralized or distributed/cloud-based. In some implementations, the healthcare management server 120 may include one or more virtual servers, which operate in a host server environment and access the physical hardware of the host server including, for example, a processor, a memory, applications, a database, storage, network interfaces, etc., via an abstraction layer (e.g., a virtual machine manager). In some implementations, the healthcare management server 120 may be a Hypertext Transfer Protocol (HTTP) server, a Representational State Transfer (REST) service, or other server type, having structure and/or functionality for processing and satisfying content requests and/or receiving content from one or more of the client devices 115, the plurality of data sources 135, and the plurality of third-party servers 140 that are coupled to the network 105.

Also, instead of or in addition, the healthcare management server 120 may implement its own application programming interface (API) for the transmission of instructions, data, results, and other information between the server 120 and other entities communicatively coupled to the network 105. For example, the API may be a software interface exposed over the HTTP protocol by the healthcare management server 120. The API exposes internal data and functionality of the service hosted by the healthcare management server 120 to API requests originating from one or more of the intelligent message handling application 110, the plurality of data sources 135, and the plurality of third-party servers 140. In one example, the intelligent message handling application 110b implemented by the healthcare management server 120 receives messages from the client devices 115 and sends information and action requests in response. In some implementations, the intelligent message handling application 110b passes an authenticated request including a set of parameters for information to one or more of the third-party servers 140 and the data source 135 and receives an object (e.g., XML or JSON) with associated results. In some implementations, the healthcare management server 120 may also include a database coupled to it (e.g., over the network 105) to store structured data in a relational database and a file system (e.g., HDFS, NFS, etc.) for unstructured or semi-structured data. In some implementations, the healthcare management server 120 may include an instance of a data store that stores various types of data for access and/or retrieval by the intelligent message handling application 110. For example, the data store may store machine learning models for natural language understanding of user intents, actions associated with messages, and other information as will be described below. Other types of user data are also possible and contemplated.

In some implementations, the healthcare management server 120 sends and receives messages and data to and from other entities of the system 100 via the network 105. For example, the healthcare management server 120 sends and receives messages including instructions to and from the client device 115. In some implementations, the healthcare management server 120 may serve as a middle layer and permit interactions between the client device 115 and the plurality of the third-party servers 140 and the data sources 135 to flow through and from the healthcare management server 120 for security and convenience. In some implementations, the healthcare management server 120 may be operable to receive a message or series of messages from a client device 115, determine user intent from those messages using an artificial intelligence platform, and initiate an action that is responsive to the message or messages. For example, if the message intent is for appointment request, the healthcare management server 120 processes the appointment request based on the user context and hospital resource availability, and generates and sends a reply message with a recommended appointment for treating a patient health condition determined from the message or messages, etc. The healthcare management server 120 may send data to and receive data from the other entities of the system 100 via the network 105. It should be understood that the healthcare management server 120 is not limited to providing the above-noted acts and/or functionality and may include other network-accessible services. In addition, while a single healthcare management server 120 is depicted in FIG. 1, it should be understood that there may be any number of healthcare management servers 120 or a server cluster.

Each of the one or more third-party servers 140 may be, or may be implemented by, a computing device including a processor, a memory, applications, a database, and network communication capabilities. A third-party server 140 may be a Hypertext Transfer Protocol (HTTP) server, a Representational State Transfer (REST) service, or other server type, having structure and/or functionality for processing and satisfying content requests and/or requesting and receiving content from one or more of the client devices 115, the data sources 135, and the healthcare management server 120 that are coupled to the network 105. In some implementations, the third-party server 140 may include an online service 111 dedicated to providing access to various services and information resources hosted by the third-party server 140 via web, mobile, enterprise, and/or cloud applications. The online service 111 may obtain and store user data, user-generated data, content items (e.g., videos, text, images, etc.), and interaction data reflecting the interaction of users with the content items. In some implementations, the third-party server 140 may provide an API 136 to facilitate access of the third-party server 140 by one or more of the client devices 115, the data sources 135, and the healthcare management server 120 that are coupled to the network 105. User-generated data, as described herein, may include one or more of user profile information (e.g., user id, user preferences, user history, social network connections, primary care physicians, etc.), logged information (e.g., heart rate, activity metrics, sleep quality data, calories and nutrient data, user device specific information, historical actions, medication history, etc.), and other user specific information. In some implementations, the online service 111 allows users to share content with other users (e.g., friends, contacts, public, similar users, primary care physicians, clinical staff, administrative staff, etc.), purchase and/or view items (e.g., e-books, videos, music, games, subscription, fitness products, prescription refill, laboratory results, etc.), and other similar actions. For example, the online service 111 may provide various services such as digital fitness content; personal training; running and cycling tracking service; music streaming service; mobile health (mHealth) service; video streaming service; web mapping service; multimedia messaging service; electronic mail service; a calendar service; news service; news aggregator service; social networking service; location-based service; photo and video-sharing social networking service; sleep-tracking service; diet-tracking and calorie counting service; ridesharing service; online banking service; online information database service; travel service; online e-commerce marketplace; ratings and review service; restaurant-reservation service; food delivery service; search service; health and fitness service; home automation and security service; Internet of Things (IoT), multimedia hosting, distribution, and sharing service; cloud-based data storage and sharing service; a scheduling service; an enterprise clinical workflow service; a combination of one or more of the foregoing services; or any other service where users retrieve, collaborate, and/or share information, etc. It should be noted that the list of items provided above as examples for the online service 111 above are not exhaustive and that others are contemplated in the techniques described herein.

Each of the plurality of data sources 135 may be, or may be implemented by, a computing device including a processor, a memory, applications, a database, and network communication capabilities. In some implementations, the data sources may be a data warehouse, a system of record (SOR), or belonging to a data repository owned by an organization that provides real-time or close to real-time data automatically or responsive to being polled or queried by the healthcare management server 120. Each of the plurality of data sources 135 may be associated with a first-party entity (e.g., server 120) or third-party entity (e.g., server 140 associated with a separate company or service provider), such as a health insurance organization, a health care organization, world health organization, an independent healthcare provider, a healthcare-related call center or customer service company, a healthcare software company, an Electronic Medical Record (EMR) software company, an Electronic Health Record (EHR) software company, a pharmacy management system, a drug research institute, a patient management software system, a clinical decision support system, a clinical workflow management system, a scheduling system, a patient-satisfaction measurement firm, a medication adherence tracking system, a public-records database, a data mining platform, a Software as a Service (SaaS) data analytics company, a data science and machine learning platform, news site, support groups, health blogs, etc. Examples of data provided by the plurality of data sources 135 may include, but is not limited to, pharmacy data, physician-patient encounter data, clinical data, patient data, EMR, EHR, patient diagnosis data, patient procedures, appointment notes, socioeconomic data, social determinant data, demographic data, health plan data, prescription data, call center data, appointment schedule data, disposition data, calendar data, medication data, pharmaceutical data, survey data, medication adherence data, machine learning models, machine learning-based data analysis results, etc. In some implementations, each of the plurality of data sources 135 may be configured to provide or facilitate an API (not shown) that allows the intelligent message handling application 110 to access data and information for performing the functionality described herein.

The intelligent message handling application 110 may include software and/or logic to provide the functionality for intelligent message intent detection, routing, and processing for delivering the appropriate healthcare services. In some implementations, the intelligent message handling application 110 may be implemented using programmable or specialized hardware, such as a field-programmable gate array (FPGA) or an application-specific integrated circuit (ASIC). In some implementations, the intelligent message handling application 110 may be implemented using a combination of hardware and software. In one implementation, the intelligent message handling application 110b is stored and executed on healthcare management server 120 alone. In another implementation, the intelligent message handling application 110a, 110n is stored and executed on client device 115 alone. In other implementations, the intelligent message handling application 110 may be stored and executed on various combinations of the client device 115, the data sources 135, the third-party servers 140, and the healthcare management server 120.

In some implementations, the intelligent message handling application 110a may be a thin-client application with some functionality executed on the client device 115 and additional functionality executed on the healthcare management server 120 by the intelligent message handling application 110b. In some implementations, the intelligent message handling application 110 may generate and present various user interfaces to perform these acts and/or functionality, which may in some cases be based at least in part on information received from the healthcare management server 120, the client device 115, one or more of the third-party servers 140 and/or the data sources 135 via the network 105. In some implementations, the intelligent message handling application 110 is code operable in a web browser, a web application accessible via a web browser, a native application (e.g., mobile application, installed application, etc.) on the client device 115, a combination thereof, etc. Additional structure, acts, and/or functionality of the intelligent message handling application 110 is further discussed below with reference to at least FIG. 2.

In some implementations, the intelligent message handling application 110 may require users to be registered with the healthcare management server 120 to access the acts and/or functionality described herein. For example, to access various acts and/or functionality provided by the intelligent message handling application 110, the intelligent message handling application 110 may require a user to authenticate his/her identity. For example, the intelligent message handling application 110 may require a user seeking access to authenticate their identity by inputting credentials in an associated user interface. In another example, the intelligent message handling application 110 may interact with a federated identity server (not shown) to register and/or authenticate the user by scanning and verifying biometrics including username and password, facial attributes, fingerprint, and voice.

Other variations and/or combinations are also possible and contemplated. It should be understood that the system 100 illustrated in FIG. 1 is representative of an example system and that a variety of different system environments and configurations are contemplated and are within the scope of the present disclosure. For example, various acts and/or functionality may be moved from a server 120 to a client device 115, or vice versa, data may be consolidated into a single data store or further segmented into additional data stores, and some implementations may include additional or fewer computing devices, services, and/or networks, and may implement various functionality client or server-side. Furthermore, various entities of the system may be integrated into a single computing device or system or divided into additional computing devices or systems, etc.

Figure 2:
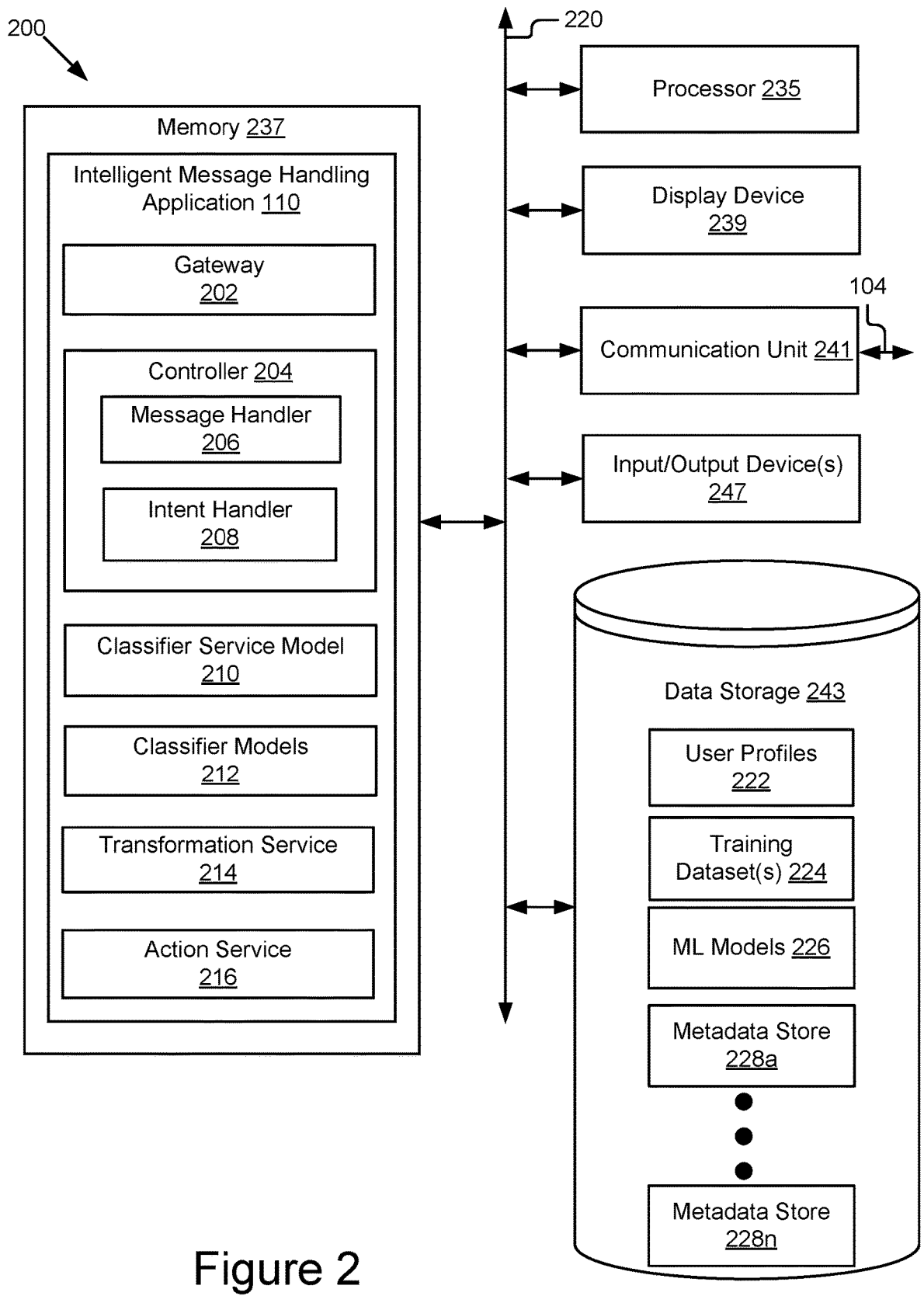
FIG. 2 is a block diagram illustrating one implementation of a computing device including an intelligent message handling application.

FIG. 2 is a block diagram illustrating one implementation of a computing device 200 including an intelligent message handling application 110. The computing device 200 may also include a processor 235, a memory 237, a display device 239, a communication unit 241, an input/output device(s) 247, and a data storage 243, according to some examples. The components of the computing device 200 are communicatively coupled by a bus 220. In some implementations, the computing device 200 may be representative of the client device 115, the healthcare management server 120, or a combination of the client device 115 and the healthcare management server 120. In such implementations where the computing device 200 is the client device 115 or the healthcare management server 120, it should be understood that the client device 115 and the healthcare management server 120 may take other forms and include additional or fewer components without departing from the scope of the present disclosure. For example, while not shown, the computing device 200 may include sensors, capture devices, additional processors, and other physical configurations. Additionally, it should be understood that the computer architecture depicted in FIG. 2 could be applied to other entities of the system 100 with various modifications, including, for example, the servers 140 and data sources 135.

The processor 235 may execute software instructions by performing various input/output, logical, and/or mathematical operations. The processor 235 may have various computing architectures to process data signals including, for example, a complex instruction set computer (CISC) architecture, a reduced instruction set computer (RISC) architecture, and/or an architecture implementing a combination of instruction sets. The processor 235 may be physical and/or virtual and may include a single processing unit or a plurality of processing units and/or cores. In some implementations, the processor 235 may be capable of generating and providing electronic display signals to a display device 239, supporting the display of images, capturing, and transmitting images, and performing complex tasks including various types of feature extraction and sampling. In some implementations, the processor 235 may be coupled to the memory 237 via the bus 220 to access data and instructions therefrom and store data therein. The bus 220 may couple the processor 235 to the other components of the computing device 200 including, for example, the memory 237, the communication unit 241, the display device 239, the input/output device(s) 247, and the data storage 243.

The memory 237 may store and provide access to data for the other components of the computing device 200. The memory 237 may be included in a single computing device or distributed among a plurality of computing devices as discussed elsewhere herein. In some implementations, the memory 237 may store instructions and/or data that may be executed by the processor 235. The instructions and/or data may include code for performing the techniques described herein. For example, as depicted in FIG. 2, the memory 237 may store the intelligent message handling application 110. The memory 237 is also capable of storing other instructions and data, including, for example, an operating system, hardware drivers, other software applications, databases, etc. The memory 237 may be coupled to the bus 220 for communication with the processor 235 and the other components of the computing device 200.

The memory 237 may include one or more non-transitory computer-usable (e.g., readable, writeable) device, a static random access memory (SRAM) device, a dynamic random access memory (DRAM) device, an embedded memory device, a discrete memory device (e.g., a PROM, FPROM, ROM), a hard disk drive, an optical disk drive (CD, DVD, Blu-ray™, etc.) mediums, which can be any tangible apparatus or device that can contain, store, communicate, or transport instructions, data, computer programs, software, code, routines, etc., for processing by or in connection with the processor 235. In some implementations, the memory 237 may include one or more of volatile memory and non-volatile memory. It should be understood that the memory 237 may be a single device or may include multiple types of devices and configurations.

The bus 220 may represent one or more buses including an industry standard architecture (ISA) bus, a peripheral component interconnect (PCI) bus, a universal serial bus (USB), or some other bus providing similar functionality. The bus 220 may include a communication bus for transferring data between components of the computing device 200 or between computing device 200 and other components of the system 100 via the network 105 or portions thereof, a processor mesh, a combination thereof, etc. In some implementations, the intelligent message handling application 110 and various other software operating on the computing device 200 (e.g., an operating system, device drivers, etc.) may cooperate and communicate via a software communication mechanism implemented in association with the bus 220. The software communication mechanism may include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication may be configured to be secure (e.g., SSH, HTTPS, etc.).

The display device 239 may be any conventional display device, monitor or screen, including but not limited to, a liquid crystal display (LCD), light emitting diode (LED), organic light-emitting diode (OLED) display or any other similarly equipped display device, screen, or monitor. The display device 239 represents any device equipped to display user interfaces, electronic images, and data as described herein. In some implementations, the display device 239 may output display in binary (only two different values for pixels), monochrome (multiple shades of one color), or multiple colors and shades. The display device 239 is coupled to the bus 220 for communication with the processor 235 and the other components of the computing device 200. In some implementations, the display device 239 may be a touch-screen display device capable of receiving input from one or more fingers of a user. For example, the display device 239 may be a capacitive touch-screen display device capable of detecting and interpreting multiple points of contact with the display surface. In some implementations, the computing device 200 (e.g., client device 115) may include a graphics adapter (not shown) for rendering and outputting the images and data for presentation on display device 239. The graphics adapter (not shown) may be a separate processing device including a separate processor and memory (not shown) or may be integrated with the processor 235 and memory 237.

The input/output (I/O) device(s) 247 may include any standard device for inputting or outputting information and may be coupled to the computing device 200 either directly or through intervening I/O controllers. In some implementations, the input device 247 may include one or more peripheral devices. Non-limiting example I/O devices 247 include a touch screen or any other similarly equipped display device equipped to display user interfaces, electronic images, and data as described herein, a touchpad, a keyboard, a scanner, a stylus, an audio reproduction device (e.g., speaker), a microphone array, a barcode reader, an eye gaze tracker, a sip-and-puff device, and any other I/O components for facilitating communication and/or interaction with users. In some implementations, the functionality of the input/output device 247 and the display device 239 may be integrated, and a user of the computing device 200 (e.g., client device 115) may interact with the computing device 200 by contacting a surface of the display device 239 using one or more fingers. For example, the user may interact with an emulated (i.e., virtual, or soft) keyboard displayed on the touch-screen display device 239 by using fingers to contact the display in the keyboard regions.

The communication unit 241 is hardware for receiving and transmitting data by linking the processor 235 to the network 105 and other processing systems via signal line 104. The communication unit 241 receives data such as message from the client device 115 and transmits the message to the intelligent message handling application 110, for example, an e-mail, a post, a text, website input, a mobile application, a phone call, interactive voice response (IVR), instant messaging chat, etc. The message may provide information about a condition or request for service from a healthcare provider. The communication unit 241 also transmits information including media to the client device 115 for display, for example, in response to the request. The communication unit 241 is coupled to the bus 220. In some implementations, the communication unit 241 may include a port for direct physical connection to the client device 115 or to another communication channel. For example, the communication unit 241 may include an RJ45 port or similar port for wired communication with the client device 115. In other implementations, the communication unit 241 may include a wireless transceiver (not shown) for exchanging data with the client device 115 or any other communication channel using one or more wireless communication methods, such as IEEE 802.11, IEEE 802.16, Bluetooth® or another suitable wireless communication method.

In yet other implementations, the communication unit 241 may include a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still other implementations, the communication unit 241 may include a wired port and a wireless transceiver. The communication unit 241 also provides other conventional connections to the network 105 for distribution of files and/or media objects using standard network protocols such as TCP/IP, HTTP, HTTPS, and SMTP as will be understood to those skilled in the art.

The data storage 243 is a non-transitory memory that stores data for providing the functionality described herein. In some implementations, the data storage 243 may be coupled to the components 235, 237, 239, 241, 243, and 247 via the bus 220 to receive and provide access to data. In some implementations, the data storage 243 may store data received from other elements of the system 100 including, for example, entities 135, 140, and/or the intelligent message handling application 110, and may provide data access to these entities. The data storage 243 may store, among other data, user profiles 222, training datasets 224, machine learning models 226, and one or more metadata stores 228a-228n. The data stored in the data storage 243 is described below in more detail.

The data storage 243 may be included in the computing device 200 or in another computing device and/or storage system distinct from but coupled to or accessible by the computing device 200. The data storage 243 may include one or more non-transitory computer-readable mediums for storing the data. In some implementations, the data storage 243 may be incorporated with the memory 237 or may be distinct therefrom. The data storage 243 may be a dynamic random-access memory (DRAM) device, a static random-access memory (SRAM) device, flash memory, or some other memory devices. In some implementations, the data storage 243 may include a database management system (DBMS) operable on the computing device 200. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations. In other implementations, the data storage 243 also may include a non-volatile memory or similar permanent storage device and media including a hard disk drive, a CD-ROM device, a DVD-ROM device, a DVD-RAM device, a DVD-RW device, a flash memory device, or some other mass storage device for storing information on a more permanent basis.

The user profile 222 may include data and insights about the user including name, unique user identifier, age, gender, interests, height, weight, risk score, location, profile photo, recently measured vital signs, diagnosed conditions (e.g., diabetic, mental health, heart attack, etc.), medical history, user preferences (e.g., phone call for upcoming reminders, etc.), appointment preferences (e.g., video call for virtual urgent care visits, etc.), prescription (e.g., refill dates, etc.), laboratory test results, treatment or care plans, fitness goals (e.g., gain physical mobility, lose weight, etc.), activities (e.g. number of physical therapy sessions, number of missed appointments, synced wearable fitness devices, synced third-party mobile Health applications, etc.), etc.

The training datasets 224 include data that can be used to train the various models in the intelligent message handling application 110. For example, the training data sets 224 can be used to train the client service model and the classify models. For example, any data received by the gateway 202 can be processed and curated to produce training data sets 224. Example training datasets 224 may include, but are not limited to, a dataset containing utterances of historical multilingual user input with a labelled health or urgent disease condition as output to predict, a dataset of health condition identification hints and patterns, a dataset of appointment booking data for different scripts or reasons for appointment (e.g., rash, physical exam, flu, etc.), a dataset of appointment booking data for different modalities of appointment (e.g., video call, phone call, in-person visit, text-based urgent care, etc.), a dataset of appointment booking data for patient members of different age groups (e.g., 0-18, 18-45, 45-65, 65+), a dataset of appointment booking data for patient members of different demographics, a dataset of patient member profiles and patient dispositions for the member profiles, a dataset of medical dictionary terms and indexed search terms, a dataset of patient member profiles and appointment modality of recent bookings for the member profiles, a dataset of clinical context (e.g., past and current health conditions, medications, allergies, laboratory results, treatments, historical encounter data, current encounter data, etc.) for a number of patient members, etc. In some implementations, the training dataset 224 may be created from crowd source data. For example, in the instance where a user (e.g., patient member) consents to use of their data for creating a training dataset, the data can be forwarded and the aggregated by remotely located reviewers to review the data, identify a segment of the data, classify and provide a label for the identified data segment. The training datasets 224 is stored in the data storage 243.

In some implementations, the machine learning models 226 may be a neural network model and includes a layer and/or layers of memory units where memory units each have corresponding weights. A variety of neural network models may be utilized including feed forward neural networks, convolutional neural networks (CNN), recurrent neural networks, radial basis functions, other neural network models, as well as combinations of several neural networks. Additionally, the machine learning model 226 may represent a variety of other machine learning techniques in addition to neural networks, for example, support vector machines, decision trees, Bayesian networks, random decision forests, k-nearest neighbors, linear regression, least squares, hidden Markov models, other machine learning techniques, and/or combinations of machine learning techniques. For example, the machine learning model 226 may be a trained natural language understanding (NLU) model that is able to classify user input utterance (e.g., text or speech) and one or more of patient member profile, past medical and clinical history, user interaction history on different channels, demographic data, etc. to identify intent of messages (e.g., with a classification score) of a patient member, intent to schedule, reschedule or cancel an appointment, intent to refill a medical prescription, patient validation, status check, referral, information retrieval, COVID screening, location, leave a message for a primary care physician, etc. The one or more machine learning models 226 may also supporting multi-lingual input classification. For example, the NLU models may be trained to be native language-specific and extended to support multi-lingual user inputs in English, Spanish, Vietnamese, Russian, etc. In another example, the machine learning models 226 perform language translation of user inputs. In other examples, the NLU models may be trained based on the following features or attributes, including but not limited to: patient member profile (age, gender, location, race, socioeconomic, etc.); patient member clinical context (e.g., past and current health conditions, medications, allergies, laboratory results, treatments, historical encounter data, current encounter data, etc.); medical terms and dictionary; or statistics of input text, predicted disease conditions, proposed and actual dispositions. In some implementations, the NLU model is augmented or enhanced with a knowledge base that includes a medical dictionary, index search terms and associated dispositions for those terms. The knowledge base may also be enhanced to include data such as text input matches to text input frequency, disease frequency, drift between prediction and actual disposition, disease severity, patient member profile (e.g., age, gender, location, language, and other demographic data, etc.), physician or subject matter expert inputs.

The one or more metadata stores 228a-228n store metadata relating to each message and its disposition. For example, there are a variety of different metastores that are utilized by the intelligent message handling application 110 for different stages in its operation. Each metastore keeps track of all messages received and their disposition for that specific stage of processing. In some implementations, the system 100 includes a gateway metastore, a controller metastore (design time), a controller metastore (runtime), the classifier ops megastore, and an action response megastore. It should be understood that additional metastores may be provided as needed to store information about the processing of each message at each stage. It should also be understood that the data in the metastores may be combined for fewer meta-stores than just listed. In some implementations, the one or more data stores 228a-228n are stored in the data storage 243.

It should be understood that other processors, operating systems, sensors, displays, and physical configurations are possible.

As depicted in FIG. 2, the memory 237 may include the intelligent message handling application 110. In some implementations, the intelligent message handling application 110 may be configured to implement a secure HTTP API (not shown) to facilitate receipt and transmission of messages via the web, mobile, enterprise, and/or cloud applications for providing patients with access to care for appropriate healthcare services.

In some implementations, the intelligent message handling application 110 may include a gateway 202, a controller 204 having a message handler 206 and an intent handler 208, a classifier service module 210, classifier models 212, a transformation service 214, and an action service 216. The components 202, 204, 206, 208, 210, 212, 214 and 216 may be communicatively coupled by the bus 220 and/or the processor 235 to one another and/or the other components 237, 239, 241, 243, and 247 of the computing device 200 for cooperation and communication. The components 202, 204, 206, 208, 210, 212, 214 and 216 may each include software and/or logic to provide their respective functionality. In some implementations, the components 202, 204, 206, 208, 210, 212, 214 and 216 may each be implemented using programmable or specialized hardware including a field-programmable gate array (FPGA) or an application-specific integrated circuit (ASIC). In some implementations, the components 202, 204, 206, 208, 210, 212, 214 and 216 may each be implemented using a combination of hardware and software executable by the processor 235. In some implementations, each one of the components 202, 204, 206, 208, 210, 212, 214 and 216 may be sets of instructions stored in the memory 237 and configured to be accessible and executable by the processor 235 to provide their acts and/or functionality. In some implementations, the components 202, 204, 206, 208, 210, 212, 214 and 216 may send and receive data, via the communication unit 241, to and from one or more of the client devices 115, the healthcare management server 120, the data sources 135, and third-party servers 140. The operation and interaction of the gateway 202, the controller 204, the message handler 206, the intent handler 208, the classifier service module 210, the classifier models 212, the transformation service 214, and the action service 216 will be described in more detail below with reference to FIGS. 4-9.

Figure 3:
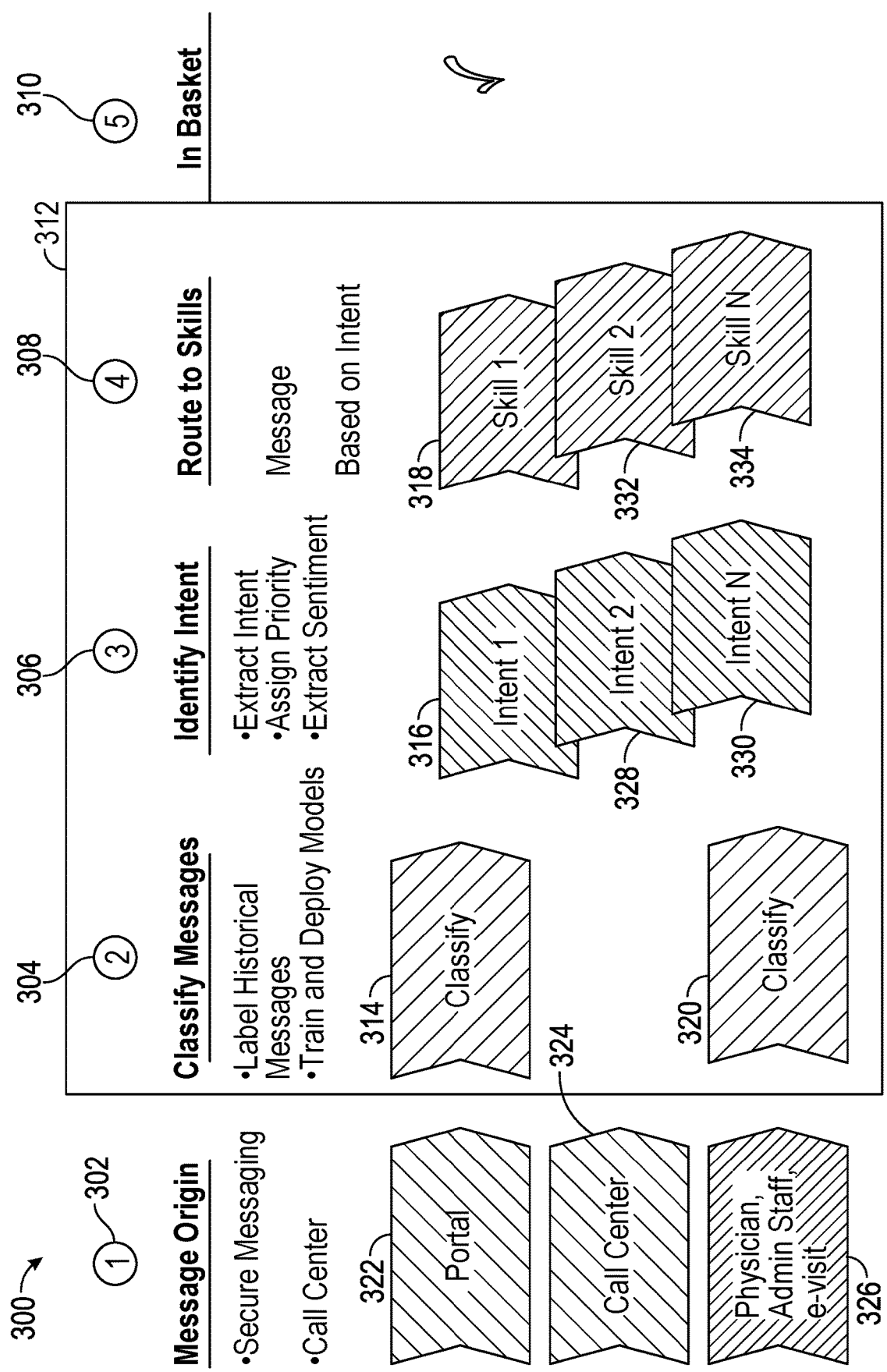
FIG. 3 is a high-level block diagram showing the processing of messages by the intelligent message handling application.

Referring now to FIG. 3, an overview of the operation and processing stages of the intelligent message handling application 110 is shown in detail. The processing stages shown in FIG. 3 are both for configuration and setup of the intelligent message handling application 110 as well as its operation. The intelligent message handling application 110 advantageously processes incoming messages to determine user intent and sentiment, and based on user intent, routes the messages to the appropriately for the action and skill need to respond to the message, as well as automatically prioritizing the messages for processing.

In a first stage 302, messages are received from users. In particular, the messages can be received by the gateway 202 and stored for later use, as well as processed. As noted in FIG. 3 and above, the messages may include various forms of secure messaging or interaction with a call center, including but not limited to, an email, a post, a text, website input, a mobile application, a phone call, interactive voice response (IVR), instant messaging chat, etc. As illustrated, the messages may be provided by the user directly via portal 322, from a user via a third-party system, such as representative in a call center 324 or by any medical personnel or administrative staff 326 using secure computing facilities or their individual computing devices 115. The messages, in whatever form, are then provided from the first stage 302 to a second stage 304.

In the second stage 304, the messages are classified. In one implementation for configuration and setup of the intelligent message handling application 110, the messages are classified to train and deploy AI/ML models. For example, the messages may be classified by labeling historical messages based on their content. A series of labels can be applied to each message depending on which labels each message satisfies. In some implementations, this is a manual process, but it can be done programmatically with automatic labeling techniques. For example, a list of topics may be identified using various methods, such as classification techniques using training datasets. Once the historical messages have been classified or labelled, the data can be used to train the AI/ML model to create it. Once the AI/ML model has been created, it can classify incoming messages by processing the incoming messages and applying a predicted set of labels based on the model. As shown in FIG. 3, messages received from portal 322 may be classified 314 using the AI/ML model. As also shown in FIG. 3, messages received from a call center 324 or through physician, admin staff, or e-visit 326 are also classified 320. The model will output one or more classifications for each message it processes. Once the messages are processed by the second stage 304, processing continues by the third stage 306.

In the third stage 306, the intelligent message handling application 110 processes incoming messages with one or more AI/ML models to extract the intent and the sentiment of the message. In some implementations, a first AI/ML model is used for extracting intent, and a second different AI/ML model is used for extracting sentiment. In some implementations, a single AI/ML model can be used for extracting both intent and sentiment. It should be understood that the process can be further improved in speed and accuracy by having multiple AI/ML models for different intents and sentiments. During the third stage 306, the intelligent message handling application 110 also assigns a priority in processing to each message. A priority may be tiered, such as low, medium, or high, in an embodiment. In other embodiments, other priority levels may be used, such as non-urgent, urgent, and very urgent. The priority assigned to each message can be based upon a number of factors including the center, the recipient, the content, the extracted intent, the extracting sentiment, or other features. In an embodiment, a priority may be assigned based on a separate AI/ML model that has been trained to classify messages based on these features. As illustrated in FIG. 3, a first intent 316 may be extracted by an AI/ML model. A second intent 328 may be extracted by the same AI/ML model, or by a different model. Any number of intents 330 may be extracted by the same or different models, in an embodiment. Although not illustrated, sentiments and priorities may also be extracted and/or assigned, similarly to intents. Once the intent, sentiment, and priority have been determined for a given message, processing of the message continues onto a fourth stage 308.

In the fourth stage 308, the messages are routed to different entities with different skills based upon intent. In some implementations, the intent and topic determined in the third stage 306 are added to the message. For example, a topic classifier model may be separately trained based on the content of the message, such as topics related to urgent care, pediatric care, elder care, after-surgery care, and so forth. The message may be routed to an entity having the skill to address the message based on the intent. For example, if the intent is to have a particular health condition addressed, the message is routed to the physician or medical personnel with a specialty in that health condition. As illustrated in FIG. 3, messages may be routed to entities based on intent, where the entities have a first skill 318, a second skill 332, and/or any number of skills 334. The fourth stage 308 also prioritizes the messages for processing and indicates priority to the recipient of the message based on the priority determined in the second stage 306.

In the fifth and final stage 310, the messages are transmitted to the inbox of an entity that can appropriately address the message based on the right intent, right skills, and assigned priority. For example, a very urgent message regarding prescription refills may be sent to a pharmacy department of a hospital for refilling within an hour. As another example, a non-urgent message requesting a video visit with a medical practitioner regarding a skin rash may be routed to an appointment booking system to process the request accordingly.

Figure 4:
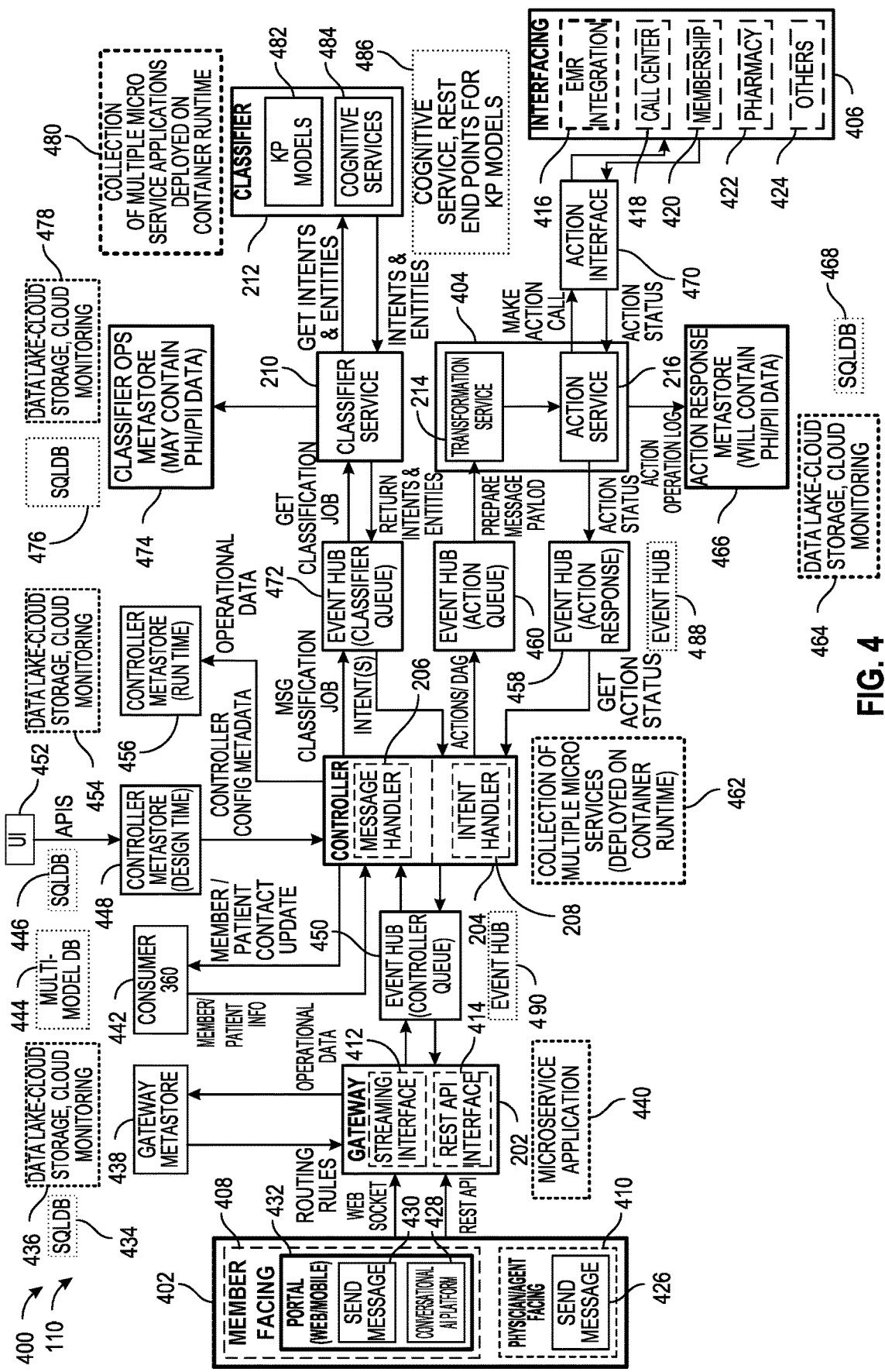
FIG. 4 is a block diagram illustrating an example implementation of the intelligent message handling application.

Referring now to FIG. 4, an example architectural implementation system 400 of the intelligent message handling application 110 is shown. As noted above, the intelligent message handling application 110 comprises the gateway 202 (including streaming interface 412 and REST API interface 414), the controller 204 (including the message handler 206 and the intent handler 208), the classifier service module 210, the classifier 212 (including models 482 and cognitive services 484), the transformation service 214, and the action service 216 in addition to other components that will now be described with reference to FIG. 4. Other components of the intelligent message handling application 110 include user interface applications 402 (including member facing applications 408 and physician/agent facing applications 410), action processing component 404 (which includes transformation 214 and action service 216), action interface 470, interfacing components 406 (including EMR integration 416, call center interface 418, membership interface 420, pharmacy interface 422, and other interfaces 424), SQL databases 434, 446, 468, & 476, data lake-cloud storage, cloud monitoring 436, 454, 464, & 478, event hubs 450, 458, 460, 472, 488, & 490, micro service applications 440, 462, & 480, cognitive services 484 & 486, rest endpoints for models 486, metastores 438, 448, 456, 466, & 474, and containers. These other components have conventional functionality as will be understood by those skilled in the art.

The gateway 202 may include software and/or logic to provide functionality for receiving, processing, and storing incoming messages, and sending, processing, and storing outgoing messages/responses. As shown in FIG. 4, the gateway 202 is coupled to receive messages from web portals 432 or applications 410. For example, messages may be received via web sockets or a REST API. The messages can be from users or patients accessing the medical services provided by the system 100 via a web or mobile portal 432 or physicians, nurses, medical personnel, or other agents using a call center application 410 of the system 100. The portal 432 may enable users to send 430 a message or may enable a conversational AI platform 428 to receive messages from and send messages to users. The gateway 202 provides a streaming interface 412 and a REST API interface 414 (as well as other APIs) for consuming applications (e.g., chat bots, email clients, text messages, etc.) to integrate with the intelligent message handling application 110. The gateway 202 is also coupled to provide operational data to a gateway metastore 438 and receive routing rules from the gateway metastore 438. The gateway metastore 438 is one of several metastores included in the intelligent message handling application 110 which will be described in more detail below. The gateway 202 is responsible for providing an interface for all incoming messages/requests (streaming and APIs). In some embodiments, the gateway 202 receives the messages and generates a unique correlation identifier (ID) for each unique message received from the consumer applications (formal and chat) or portions of the message. The correlation identifiers can be parent correlation identifiers so that information will message portions associated with parent correlation identifier can be grouped together for processing and provided to other components of the intelligent message handling application 110. The gateway 202 converts the messages to a standard payload and pushes it into a queue for the controller 204. For example, the gateway 202 is coupled by an event hub 450 to the controller 204. The event hub 450 is a bi-directional queue for sending message payloads from the gateway 202 to the controller 204 and sending response payload from the controller 204 to the gateway 202.

As noted above, the intelligent message handling application 110 may include a plurality of metastores. The metastores keep track of the messages the received and their individual disposition for each area of processing within the intelligent message handling application 110, in an embodiment. As shown in FIG. 4, there are metastores along the top and bottom of the figure, each coupled to its respective component of the intelligent message handling application. In some implementations, having multiple meta-stores (e.g., metadata stores) as depicted in the architecture of FIG. 4 allows the intelligent message handling application 110 to meet a 2-4 second service level agreement (SLA) response time. The metadata stores may include a gateway metastore 438, a controller metadata store (design time) 448, a controller metastore (runtime) 456, classifier ops megastore 474, and an action response megastore 466. The design time controller metadata store 448 includes pre-defined payload structures for each component, consumer/intent/action configuration. The metadata stores are used by each component to keep track of all messages received, their disposition, and errors and/or warnings generated by each component (e.g., operational data). Each metadata store is a combination of structured (SQLDB) and unstructured (logs) data. Each metadata store can be used with other cloud platforms, such as modern services used for well-being and reporting requirements. Metadata items in metastores may encompass any number of contextual attributes associated with users and messages within the intelligent message handling application 110.

The controller 204 may include software and/or logic for controlling the processing of received messages and generated responses by the intelligent message handling application 110. The controller 204 is coupled to send and receive messages from various event hubs. For example, the controller 204 is coupled by an event hub 450 of to the gateway 202. Similarly, the controller 204 is coupled by an event hub 472 to the classifier service 210, an event hub 460 to the transformation service 214, and an event hub 458 to the action service 216. This advantageously provides the intelligent message handling application 110 with an asynchronous architecture. In some implementations, the event hubs are Apache Kafka queues or IBM MQs. The controller 204 is coupled to a database 442 referred to as "consumer 360" to enrich the message payloads with prior contact details for any individual user from the information stored in the database. As illustrated, the controller 204 provides member/patient contact update information to the consumer 360 database 442 and receives historical member/patient information. In an embodiment, a user interface 452 may communicate, through APIs, to a controller metastore (design time) 448 that communicates various design time metadata to the controller 204, such as directed acyclic graphs (DAGs). A directed acyclic graph (DAG) is a conceptual representation of a series of activities. The order of the activities is depicted by a graph, visually presented as a set of circles, each circle representing an activity, some of which are connected by lines which represent the flow from one activity to another. In an embodiment, a DAG may be represented as programmatic code, representing a set of activities or actions to be completed in a specified order, for example. Controller configuration metadata may be received from the controller metastore (design time) 448, such as DAGs. The controller may transform this 204 and be stored as operational data in the controller metastore (run time) 456. In some implementations, the controller 204 comprises the message handler 206 and the intent handler 208 whose functionality is described below. The controller 204 is coupled to provide message classification jobs to the classifier service 210 and receive intents and entities. The controller 204 is coupled to provide actions to be performed by sending a directed acyclic graph (DAG) to the transformation service 214. The controller 204 is coupled to receive the action status from the action service 216. Based upon the source of the message received by the controller 204, the controller 204 executes the corresponding DAG to process the message. For example, based on the source, whether it be streaming message data, a voice channel, or an application providing a complete message, the controller 204 has a corresponding DAG that specifies the actions that the controller 204 will perform. For example, the DAG may specify whether intent is to be determined and what other endpoints the message information should be provided to determine intent, and what are the set of actions for the message that need to be performed. In other words, the controller 204 retrieves the DAG for the source of the message information, parses the data for the intent determination and other actions that need to be performed, and, for each of the actions, determine from the parsing and place those actions in the corresponding event hub 472 for the classifier queue or event hub 460 the action queue. Returning to an example above, a very urgent message regarding a prescription refill may be received through a phone call to a call center, where the message is sent 426 by an agent. The message is received by gateway 202, sent to the controller 204 and processed by the message handler 206 which sends the message to the classifier service 210. The classifier 212 returns the intent to refill a prescription and identify a pharmacy department of a hospital associated with the member as the entity able to perform the action. An action and DAG to refill the prescription may be sent to the event hub 460 for the action processing component 404, which may be processed by the transformation service 214 to enable an action service 216 to make an action call through an action interface 470 that eventually enables the content of the message to be sent to the identified pharmacy department 422 of the hospital for refilling the prescription with high priority, such as within an hour.

The message handler 206 may include software and/or logic to provide functionality for combining message parts and performing processing of the message. In some implementations, the message handler 206 combines (if required) all part-messages received from a consumer, constructs, or retrieves the DAG of the classification models that need to be executed, prepares the payload as per required for each model, and submits the payload to the event hub classifier queue 472. The message handler 206 is coupled to receive the member/patient information from the consumer 360 database 442 and the message handling data (e.g., intent(s) received from the classifier service 210) from the event hub 472. The message handler 206 is coupled to provide a message classification job to the event hub 472 for the classifier service 210.

The intent handler 208 may include software and/or logic to provide functionality for determining the actions to be performed on the message once the intent of the message has been determined. In some implementations, intent handler 208 prepares a DAG for pre-defined actions for each intent and submits the DAG to the transformation service 214 through the action queue of the event hub 460. This provides the ability to take action based on the detected intents. Example actions may include scheduling an appointment, refilling a prescription, receiving medical advice responsive to the message, receiving a diagnosis responsive to the message, generating questions to solicit more information response to the message, etc. The intent handler 208 is coupled to provide the DAG to the transformation service 214 via the event hub/action queue 460. The intent handler 208 is also coupled to receive an action status from the action service 216 via the action response event hub 458.

One implementation for the controller 204, the message handler 206 and the intent handler 208 are described below in more detail with reference to FIG. 5.

The classifier service module 210 may include software and/or logic to provide functionality for determining the message intent. The classifier service module 210 determines whether it needs to execute one step or multiple steps and also determines whether the steps need to be performed in serial and/or in parallel. The steps performed by the classifier service module 210 are defined in the DAG then sent from the message handler 206 to the classifier service 210. For example, classifier service 210 may call cognitive services, e.g., a Language Understanding (LUIS) model, which will perform natural language understanding (NLU) or natural language processing (NLP) to determine the intents in the message. A LUIS model may include a cloud-based conversational AI service that applies custom machine-learning intelligence to conversational and natural language text to predict overall meaning and extract relevant and detailed information. Other types of cognitive services may be used, in other embodiments. The classifier service module 210 interfaces with classifier 212 KP models 482 primarily through APIs. The classifier service module 210 retrieves messages from the classifier queue event hub 472, and then submits the message payload to the classifier 212 which uses KP models 482 and/or cognitive services 484 as defined in the DAG. The response from the classifier 212 (e.g., API response(s)) includes intents and entities that can perform the requested action (e.g., skill(s)). The response is then pushed as a message into the event hub (classifier queue) 472 for further processing by the intent handler 208.

The classifier 212 may include software and/or logic to provide functionality for determining and entities from a message or portions of it. In some accommodations, the classifier 212 utilizes natural language processing (NLP) AI/ML text classification models 482 to detect intents of the messages. The models 482 are pre-defined/pre-bills trained NLP models or pipelines that are designed to interpret the incoming messages and identify intent. In some implementations, the models 482 are deployed as a collection 480 of multiple micro service applications in container runtimes or are part of a cognitive search services platform 484. The classifier 212 is coupled to receive message payloads from the classifier service 210.

The transformation service 214 may include software and/or logic to provide functionality for transforming a message payload into a form that can be utilized by the system 400 for taking the action. The transformation service 214 is coupled to receive message payloads from the actions queue/event hub 460. In some implementations, the transformation service 214 reads payloads from the action queue and then transforms the payload into the target specific payload and then submits the target specific payload to the action service 216. The transformation service 214 is coupled to provide the target specific payload to the action service 216. For example, if the action is to get a medication refill, the action is transformed into formatting the information so that the information can be processed by the pharmacy application 422. Similarly, the transformation service 214 transforms the information and action into the proper format so that the action can be processed by the action interface subsystem 470 that will perform the action, such as retrieval of health information from an electronic medical record (EMR) through EMR integration interface 416, presentation of a message or question at a call center through call center interface 418, an action related to membership through membership interface 420, or any other systems 424 which may interface with the intelligent message handling application 110.

The action service 216 may include software and/or logic to provide functionality for interfacing with other systems or applications to perform or execute the action specified by the target specific payload. The action service 216 is coupled to receive the target specific payload from the transformation service 214. The action service 216 is responsible for interfacing with other applications that provide specific functions, such as, create an appointment, pharmacy refill request, etc. The action service 216 may make an action call to the action interface subsystem 470 to perform or execute the action, which, in response, receives the action result or response, or generates an action status. The action service 216 is coupled to provide the action result, response, or status to the action response event hub 458 for transmission back to the controller 204. The action status response may be information, such as information cards to be presented in applications, follow-up questions, responses to questions, etc. The response from the application is pushed to the action response event hub 458 queue. The action service 216 is also coupled to the action response metastore 466 for storing an action operation log. As shown in FIG. 4, the application service 216 is coupled by the action interface 470 to integrate with the service providers to take "actions" (integration with EMR, call center, membership, pharmacy, other relevant enterprise actions through various APIs, etc.).

Other implementations for the architecture of the intelligent message handling application 110 are shown and described below. These other implementations for the architecture show additional information about the subcomponents of the gateway 202, the message handler 206, the intent handler 208, the classifier service module 210, the classifier 212, the transformation service 214, and the action service 216.

Figure 5:
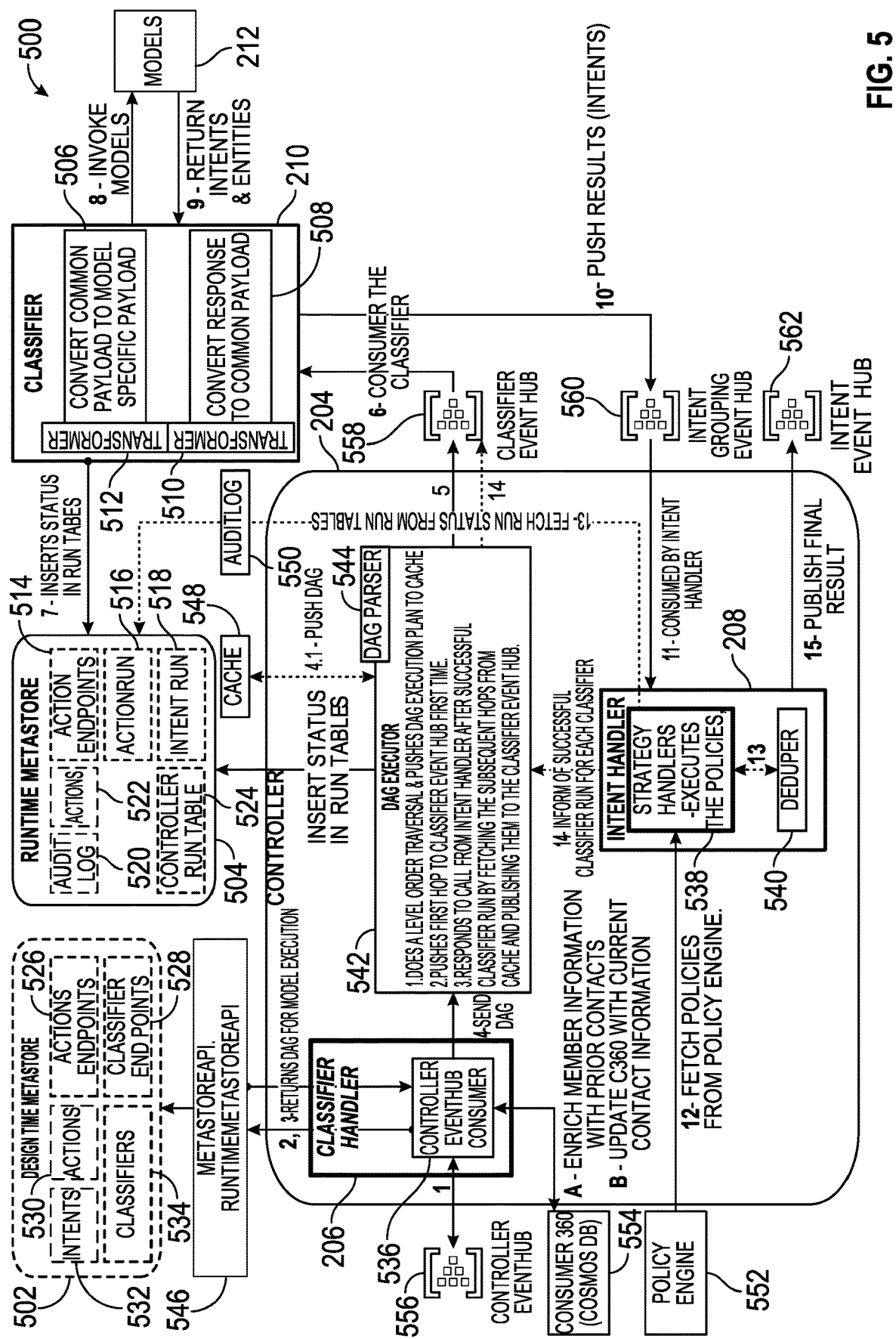
FIG. 5 is a block diagram illustrating one implementation of a controller of the intelligent message handling application.

FIG. 5 shows one example implementation of the controller 204 of the intelligent message handling application 110. The process flow 500 through the controller 204 including the message handler 206 and the intent handler 208, as well as interactions with design time metastore 502, runtime metastore 504, and classifier service 210 are described in more detail. The controller 204 prepares the DAG based on configured rules and metadata and executed. The controller 204 also keeps track of the status of each message classification job by inserting status in run tables in a runtime metastore 504 that includes an audit log 520, actions 522, action endpoints 514, action run 516, intent run 518, and a controller run table 524. The controller 204 receives intents of the messages (after being processed by the classifier service 210 and pushed to an intent grouping event hub 560) and passes them on to the intent handler 208. In an embodiment, a controller 204 includes a classifier handler 206 that includes a controller eventhub consumer 536 that is communicatively coupled to a consumer 360 (Cosmos DB) 554 where (A) member information is enriched with prior contacts and (B) the consumer 360 (Cosmos DB) 554 is updated with current contact information for a member.

FIG. 5 also shows the interaction of the controller 204 with the classifier service 210 and the models 212 (referring to the classifier 212 depicted in FIG. 4 and the associated KP models 482 and/or models called in cognitive services 484). As shown, the message (classifier) handler 206 receives (1) a message or messages portion from the controller event hub 556. The controller event hub consumer 536 of the message handler 206 provides (2) that information to the design time metastore 502 which includes intents 532, actions 530, action endpoints 526, classifiers 534 and classifier endpoints 528. The design time metastore 502 returns (3) a DAG for model execution to the message handler 206. The DAG may specify the classifier(s) that is (are) needed to process the data and their sequence of execution of classifiers. For example, there may be three groups of classifiers that may be performed in parallel with the first group being C1, C2 and then C3, the second group of classifiers being C4 then C6 and finally, the third classifiers being C5 then C11. The message (classifier) handler 206 then sends (4) the DAG to a DAG executor 542 in the controller 204. In an embodiment, the DAG executor 542 pushes (4.1) the DAG execution plan to cache 548. The DAG executor 542 sends (5) the DAG to the classifier event hub 558 and then the classifier 210 consumes (6) the classifier(s) specified in the DAG. A DAG parser 544 includes parsing functionality to digest the DAG. For example, a DAG may be formatted in programmatic code, such as a set of code instructions. In another embodiment, a DAG may be formatted in a visual format, in which actions are depicted as circles with lines (or arcs) connecting the circles. In a further embodiment, a DAG may be formatted in a textual format, in which actions are notated in a specific format. The DAG Executor 542 executes a DAG by doing (e.g., performing) a level order traversal and pushes DAG execution plan to cache 548. Next, the DAG Executor 542 pushes first hop to classifier event hub for the first time. Then, the DAG Executor 542 responds to calls from intent handler 208 after successful classifier run by fetching the subsequent hops from cache and publishing them to the classifier event hub 558.

As illustrated in FIG. 5, the classifier 210 includes a transformer 512 that converts 506 common payload to model specific payload. Additionally, the classifier 210 includes a transformer 510 that converts 508 response to common payload. The classifier 210 inserts (7) the status in the run tables of the runtime metastore 504. The classifier 210 also invokes (8) the models 212 as specified by the DAG. For example, as described above, the models 212 may refer to the KP models 482 as illustrated in FIG. 4 as well as models called by one or more cognitive services 484. The models 212 return (9) intents and entities to the classifier 210. The classifier 210 pushes (10) the intents and entities to the intent grouping event hub 560. The intent handler 208 consumes (11) the intents and entities from the intent grouping event hub 560. The strategy handlers 538 of the intent handler 208 fetches (12) policies from a policy engine 552 and subsequently executes the policies. For example, a policy to execute high priority actions within an hour may be applied to a message that is identified to include a high priority action, such as refilling a medication within an hour. The intents and entities are provided (13) to a deduper 540 while the strategy handlers 538 fetch run status from run tables in the runtime metastore 504. In an embodiment, an auditlog 550 logs the fetch run status action. For example, a run status may indicate that other actions may still be in process that are part of a DAG that has been executed in association with the message. The deduper 540 may ensure that duplicate messages with the same determined intent are "deduped" for a particular message classification job/run, in an embodiment. Then, the intent handler 208 publishes (15) the final result by sending the final result to the intent event hub 562. For example, an example intent result may be the intent of "see doctor" and a confidence level of 0.998. The intent handler 208 also informs (14) the DAG executor 542 of successful classifier runs by each classifier. The DAG executor also provides information of the successful classifier runs to the classifier event hub 558.

Figure 6:
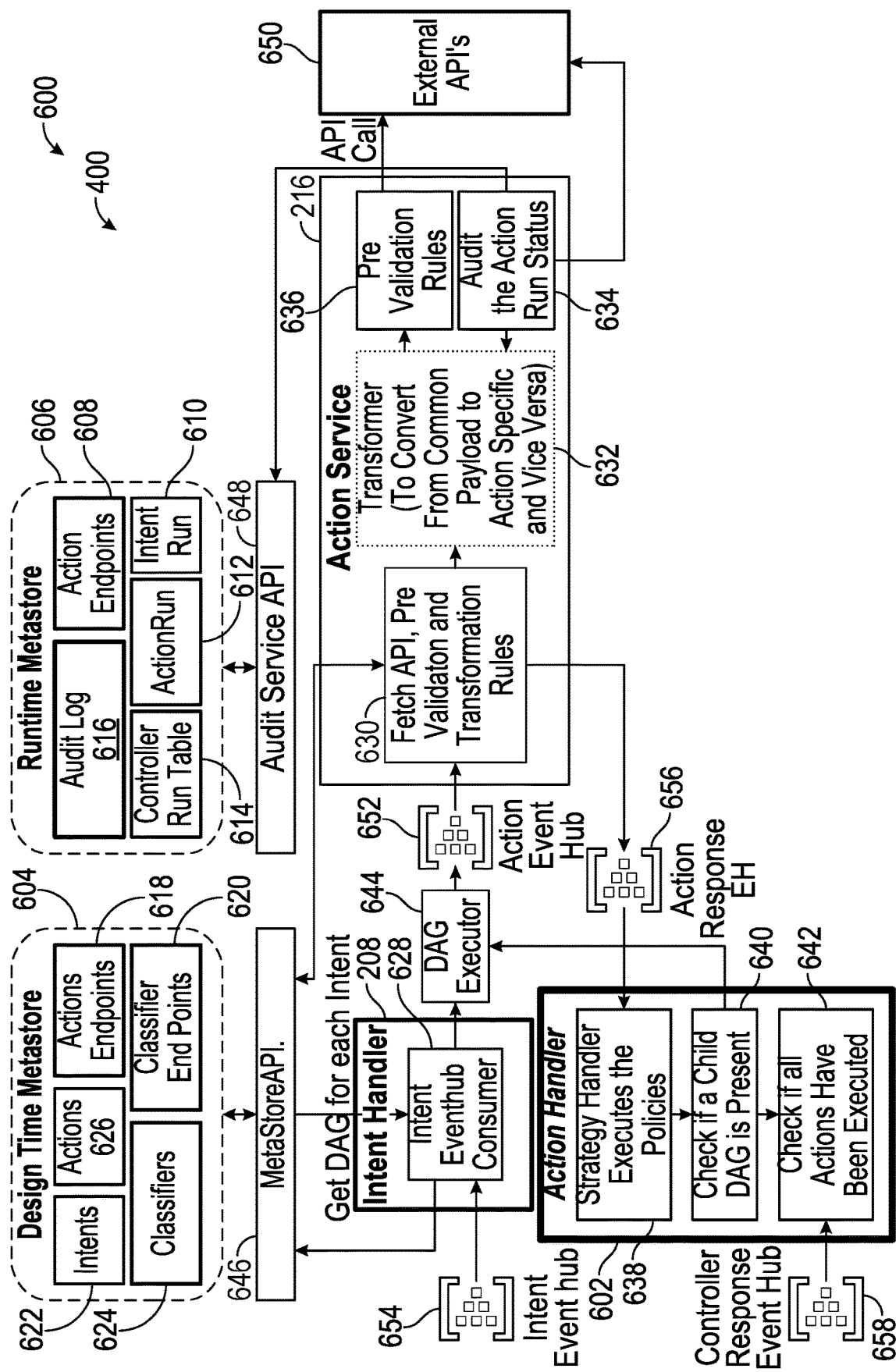
FIG. 6 is a block diagram illustrating one implementation of an action handler service performed by the intelligent message handling application.

FIG. 6 shows one implementation of an action handler service 216 performed by the intelligent message handling application 110 within the system 400 illustrated in FIG. 4, here illustrated as system 600. Once the classifier 210 has generated intent and inserted into the intent event hub 654 (as described above and illustrated in FIGS. 4 and 5), intent handler 208 consumes the intent at the Intent Eventhub Consumer 628 and begins processing. The Intent Eventhub Consumer 628 communicates information to the design time metastore 604 through a MetaStoreAPI 646, in an embodiment. The design time metastore 604 includes intents 622, classifiers 624, actions 626, actions endpoints 618, and classifier end points 620. The intent handler 208 is responsible for invoking any "action" APIs, in an embodiment. For each intent, a DAG is obtained through the MetaStoreAPI 646 by the Intent Eventhub Consumer 628, in an embodiment. The intent handler 208 passes the intent and message data to a DAG executor 644 the DAG executor 644 generates a DAG and sends the DAG to the action event hub 652. The action service 216 then consumes the DAG. The action service 216 includes software and/or instructions 630 that fetches the appropriate API to perform a particular action, the pre-validation rules for handling the particular action, and the transformation rules for executing the action using the fetched API. Then, the action service 216 transforms 632 the DAG into the system specific payload and actions. Next the action service 216 applies 636 pre-validation rules and performs an API call to the system 650 that will perform the action. For example, as described above, a message with an intent to refill a medication at a high priority may include various pre-validation rules, such as whether the prescription is still valid and has not yet expired. A pharmacy application interface may be included in the system 650 that includes external APIs, for example. A third-party system 650, in an embodiment, may include programmatic code, hardware and/or software to perform the action, such as refilling the medication within an hour. The action service 216 invokes APIs hosted by other enterprise service providers as described above and is routed as shown in FIG. 4. The system will perform the action and return the response. In an embodiment, the action service 216 audits 634 the action run status using an audit service API 648. The action service 216 performs audits on the external APIs within the system 650 performing the actions such that the response to the actions requested are transformed 632 from action specific to a common payload. In this way, it can be determined whether the actions were performed as expected. A runtime metastore 606 includes an audit log 616, action endpoints 608, IntentRun 610, ActionRun 612 and a controller run table 614. The action response event hub 656 receives the action response from the action service 216 and communicates the response to an action handler 602. An action handler 602 then consumes the response through a strategy handler 638 and applies policies to the response. The action handler 602 also checks 640 whether a child DAG is present. If so, the response and the child DAG are sent back to the DAG executor 644. If not, the action handler 602 confirms 642 that all actions have been executed by receiving pending responses from the controller response event hub 658.

Figure 7:
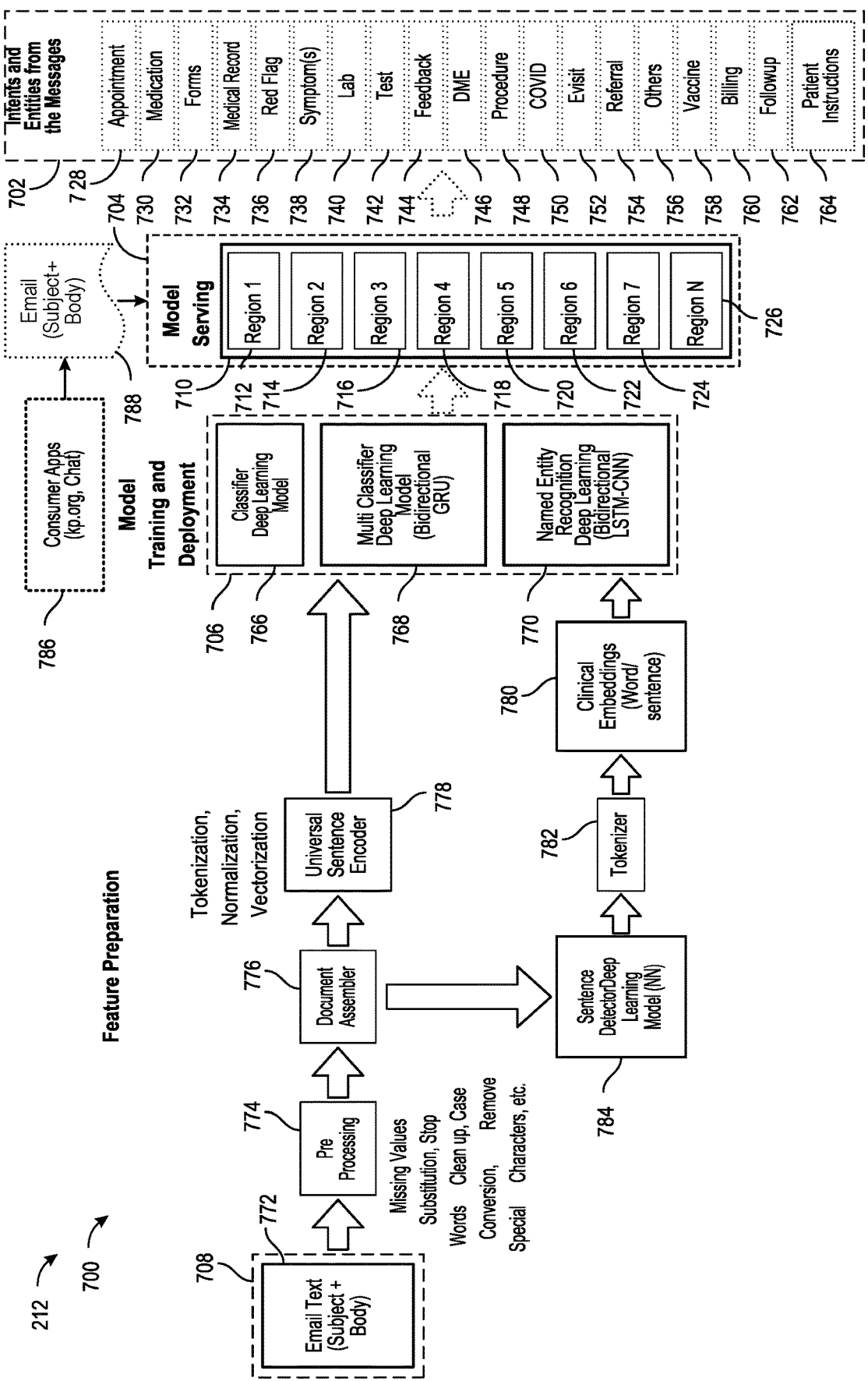
FIG. 7 is a block diagram illustrating one implementation for classifier models used by the intelligent message handling application.

FIG. 7 shows one implementation for classifier models 212 used by the intelligent message handling application 110. FIG. 7 illustrates one implementation for the classifier models 212 of the present disclosure. FIG. 7 illustrates a process 700 that begins with feature preparation for initial generation of the classifier models. For example, email text 772, which includes a subject and body, may be an example training data set 708 for an AI/ML model. Other types of training data sets 708 may be used, such as messages generated through a conversational AI platform, messages received from a portal, messages received from a third-party system that handles received telephone calls from a call center, and so forth. The classifier models 212 may be developed using utilizing healthcare specific NLP and other AI/ML libraries, in an embodiment. In other embodiments, other types of NLP libraries may be used. Feature processing further includes pre-processing 774 to identify missing values, substitution, stop words, clean up, case conversion, removal of special characters, etc. A document assembler 776 may be used to transform the data received from pre-processing 774 to annotate various parts of the message to create a document type in a particular NLP format, in an embodiment. A sentence detector deep learning model 784 may receive the message data that has been formatted as a document type, in an embodiment. The sentence detector deep learning model may use neural networks (NN) to identify sentences within a text. After sentences have been identified by the sentence detector deep learning model 784, a tokenizer 782 may be used to generate metadata that tokenizes each word, terms, symbols and/or other meaningful elements in each sentence. Then, clinical embeddings (Word/sentence) 780 may be identified based on neural networks, determining meaning of words from the context in which the word appears. For example, word embeddings model this contextual information by creating lower-dimensional space such that words that appear in similar contexts will be nearby in this new space. Clinical embeddings specifically identify words that have meaning in a clinical context, such as drug names, medical practice, hospital names, and so forth. After clinical embeddings 780 are identified, the process 700 continues to model training and deployment 706. In parallel, after a document type has been generated from the document assembler 776, a universal sentence encoder 778 may be used to perform tokenization, normalization, and vectorization of words within the message data. Various types of universal sentence encoders are available. After message data has been processed by the universal sentence encoder 778, the process 700 continues to model training and deployment 706. Models are trained with training data and deployed. Model training and deployment 706 may include a classifier deep learning model 766, a multi classifier deep learning model (such as a bidirectional Gated Recurrent Unit (GRU)) 768, and/or named entity recognition deep learning (such as a bidirectional Long Short Term Memory (LSTM)-Convolutional Neural Network (CNN)) 770. In an embodiment, models 212 are created and trained using real messages from the users that were captured and stored in the past. The models are trained to detect specific predefined intents. In some implementations, the models are trained with semi-supervised or unsupervised learning. In other examples, the models can be trained with supervised learning. Once a model has been trained and deployed 706, models can be served to process messages from a variety of consumer applications 786. FIG. 7 illustrates the model serving function 704. As illustrated, the model serving function 704 includes a region-specific model serving module 710 such that regions 1, 2, 3 . . . . N may train and deploy region-specific models 712, 714, 716, 718, 720, 722, 724, and 726. For example, a region 1 model 712 may train and deploy AI/ML models as described above for region 1 using region 1 data sets, in an embodiment. These data sets may have specific features that differ from other regions, such as hospital organizational structure, practitioner names, different entity names, third-party systems that manage vendors, and so forth. FIG. 7 also illustrates example intents and entities 702 that the models can produce by processing messages or message portions from consumer applications 786, such as an email 788 that includes a subject and body. The example list of intents and entities 702 includes an appointment 728, a medication 730, forms 732, medical record 734, red flag 736, symptom(s) 738, lab 740, test 742, feedback 744, durable medical equipment (DME) 746, procedure 748, COVID 750, evisit 752, referral 754, others (e.g., miscellaneous) 756, vaccine 758, billing 760, follow-up 762, and patient instructions 764. It should be understood that this list of intents and entities 702 is provided merely by way of example, and that additional entities and intents 702 can be derived from messages. Additional models to detect those intents and entities can also be trained, deployed, and served. In some implementations, the classifier models 212 are deployed on container runtime supported clusters.

Figure 8:
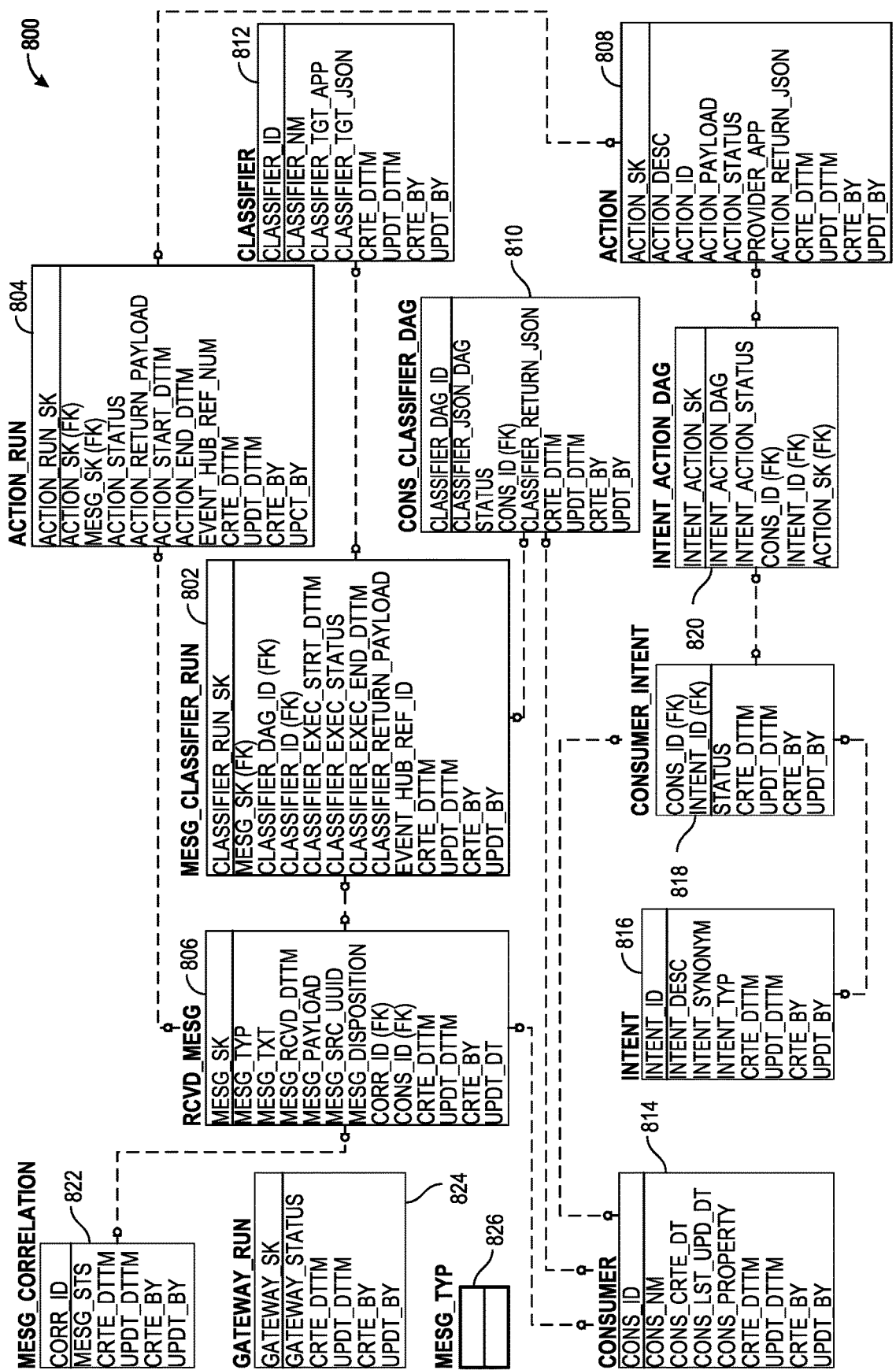
FIG. 8 is a block diagram illustrating one example implementation for a metadata model used by the intelligent message handling application.

FIG. 8 shows one example implementation for a metadata model 800 used by the intelligent message handling application 110. FIG. 8 shows the metadata data model 800 that can be used by the intelligent message handling application 110 for organizing and storing the information in a variety of metastore databases for use in determining message intent and entities. It should be understood that this metadata model 800 is provided merely by way of example, and that numerous modifications may be made to the metadata model 800 including adding, removing, and substituting any classes or constraints. The metadata model 800 as illustrated in FIG. 8 describes a database schema that depicts how data may relate to other tables or other data models. A mesg_classifier_run data model 802 may include classifier_run_sk as a primary key and mesg_sk (FK), classifier_DAG_ID (FK), classifier_ID (FK), classifier_exec_strt_dttm, classifier_exec_status, classifier_exec_end_dtm, classifier_return_payload, event_hub_ref_ID, crte_dttm, updt_dttm, crte_by, and updt_by column names describing metadata elements. "FK" may refer to a foreign key constraint, "STRT" may refer to a start, "DT™" may refer to date and time, "ID" may refer to identifier, "CRTE_BY" may refer to a process or user that created the metadata item, "UPDT_BY" may refer to a process or user that updated the metadata item, and so forth. For example, "classifier_exec_strt_dttm" may refer to a classifier's execution start date and time. An action_run data model 804 may include action_run_sk as a primary key and action_sk (FK), mesg_sk (FK), action_status, action_return_payload, action_start_dttm, action_end_dttm, event_hub_red_num, crte_dttm, uct_dttm, crte_by, and updt_by column names describing metadata elements. A rcvd_msg data model 806 may include mesg_sk as a primary key and mesg_typ, mesg_txt, mesg_rcvd_dttm, mesg_payload, mesg_src_uuid, mesg_disposition, corr_ID (FK), cons_ID (FK), crte_dttm, updt_dttm, crte_by, and updt_dt column names describing metadata elements. An action data model 808 may include action_sk as a primary key and action_desc, action_ID, action_payload, action_status, provider_app, action_return_json, crte_dttm, updt_dttm, crte_by, and updt_by column names describing metadata elements. A cons_classifier_DAG data model 810 may include classifier_DAG_ID as a primary key and classifier_json_DAG, status, cons_ID (FK), classifier_return_json, crte_dttm, updt_dttm, crte_by, and updt_by as column names describing metadata elements. A classifier data model 812 may include classifier_ID as a primary key and classifier_nm, classifier_tgt_app, classifier_tgt_json, crte_dttm, updt_dttm, crte_by, and updt_by as column names describing metadata elements. A consumer data model 814 may include cons_ID as a primary key and cons_nm, cons_crte_dt, cons_lst_upd_dt, cons_property, crte_dttm, updt_dttm, crte_by, and updt_by as column names describing metadata elements. An intent data model 816 may include intent_ID as a primary key and intent_desc, intent_synonym, intent_typ, crte_dttm, updt_dttm, crte_by, and updt_by as column names describing metadata elements. A consumer_intent data model 818 may include cons_ID (FK) and intent_ID (FK) as primary keys and status, crte_dttm, updt_dttm, crte_by, and updt_by as column names describing metadata elements. An intent_action_DAG data model 820 may include intent_action_sk as a primary key and intent_action_DAG, intent_action_status, cons_ID (FK), intent_ID (FK) and action_sk (FK) as column names describing metadata elements. A mesg_correlation data model 822 may include corr_ID as a primary key and mesg_sts, crte_dttm, updt_dttm, crte_by, and updt_by as column names describing metadata elements. A gateway_run data model 824 may include gateway_sk as primary key and gateway_status, crte_dttm, updt_dttm, crte_by, and updt_by as column names describing metadata elements. A mesg_typ data model 826 may be empty, in some implementations. In other embodiments, a mesg_typ data model 826 may include structured data, such as an email with a subject and a body text, a set of messages generated through a conversational AI platform, a set of messages from a web portal or software application, structured data received from a third-party system that describes a telephone conversation through a call center, and so forth. The different column names may refer to metadata descriptors and/or software module names that are executed to return metadata, in an embodiment. In another embodiment, a column name may refer to a code snippet of executable programmatic code.

Figure 9:
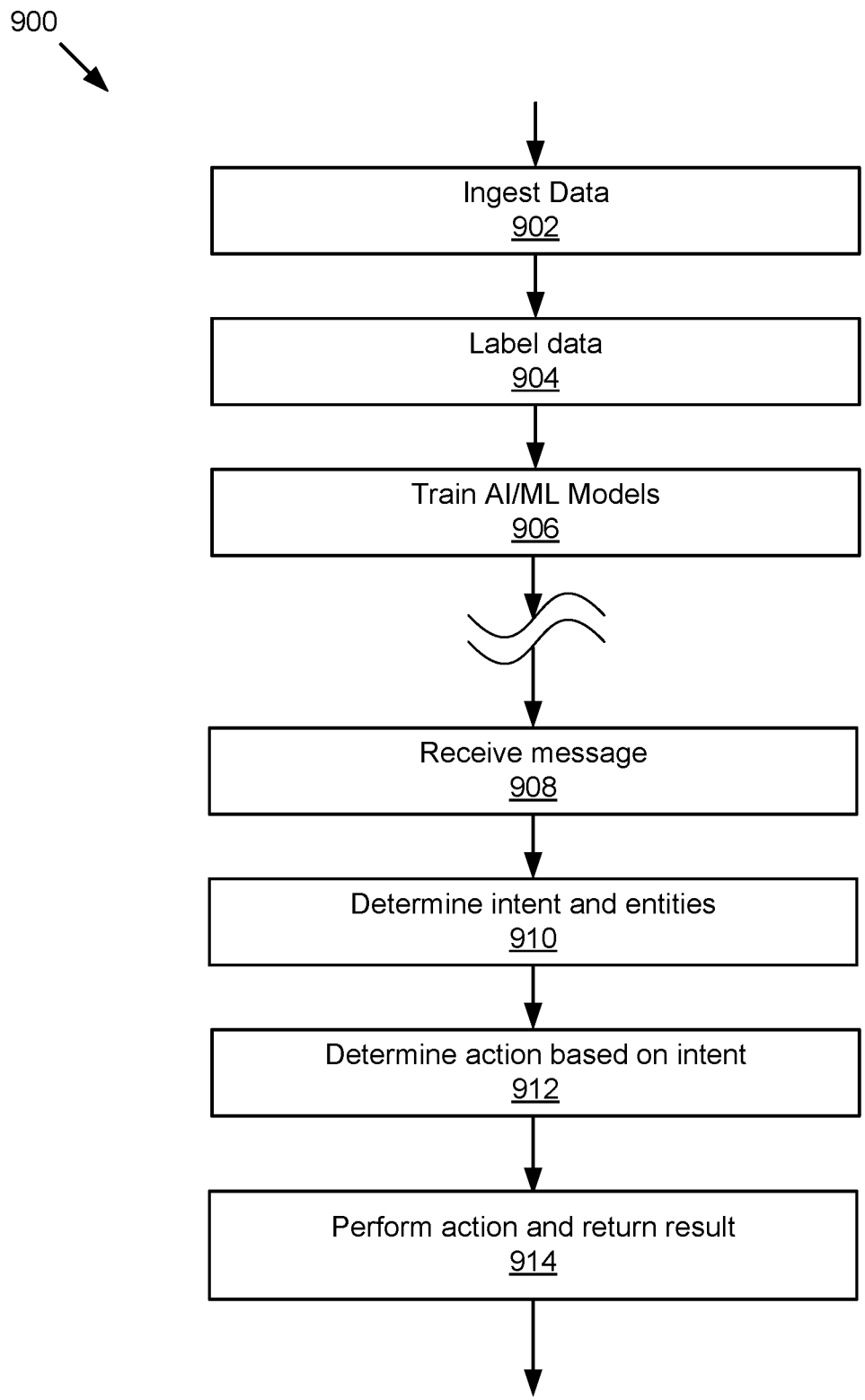
FIG. 9 is a flowchart illustrating a method for processing messages to determine message intent, message routing and actions to be performed.

FIG. 9 shows an example implementation for a method 900 for processing messages to determine message intent, message routing and actions to be performed. The method 900 begins by ingesting 902 data. In the method 900 labels 904 the ingested data. The label data is then used by the method 900 to train 906 AI/ML models. As noted above, this step may use supervised, semi-supervised or unsupervised learning to train the AI/ML models. As depicted in FIG. 9, the steps are required to create the models, and thereby configure the intelligent message handling application 110. Once these steps have been performed, messages may be applied to the models identify intent and perform actions to generate responses. The method 900 continues by receiving 908 a message or portions of it. Then, the method 900 determines 910 intent of the message and the entities related to the intent. Next, the method 900 determines 912 an action based on the determined intent a block 910. In some implementations, the action is defined by a parent DAG. Next the method 900 performs the action 914 and returns the result(s).

A system and method for intelligent message intent detection and routing for determining and providing the appropriate healthcare services has been described. In the above description, for purposes of explanation, numerous specific details are set forth in order to provide a thorough understanding of the techniques introduced above. It will be apparent, however, to one skilled in the art that the techniques can be practiced without these specific details. In other instances, structures and devices are shown in block diagram form in order to avoid obscuring the description and for ease of understanding. For example, the techniques are described in one implementation above primarily with reference to software and particular hardware. However, the present invention applies to any type of computing system that can receive data and commands, and present information as part of any peripheral devices providing services.

Reference in the specification to "one implementation" or "an implementation" means that a particular feature, structure, or characteristic described in connection with the implementation is included in at least one implementation. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are, in some circumstances, used by those skilled in the data processing arts to convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of a hardware implementation, a software implementation, or implementations containing both hardware and software elements. For instance, the technology may be implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions and/or formats.

Furthermore, the modules, routines, features, attributes, methodologies, engines, and other aspects of the disclosure can be implemented as software, hardware, firmware, or any combination of the foregoing. Also, wherever an element, an example of which is a module, of the specification is implemented as software, the element can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A computer-implemented method comprising:
receiving, through an intelligent message handling application, a message in a first format of multiple possible formats from a user;
determining, at a healthcare management server, a plurality of metadata items about the user and the message, the plurality of metadata items including at least a directed acyclic graph (DAG) describing one or more processing activities to be performed on the message, the plurality of metadata items further including a unique correlation identifier associated with the message based on the user;
generating, at the healthcare management server, a message classification job based on the plurality of metadata items about the user and the message;
processing the message classification job using one or more classifier models based on the DAG;
determining an intent of the message and one or more entities based on the processing of the message classification job;
generating an action pre-defined in the DAG to execute in association with the one or more entities based on the intent of the message and the unique correlation identifier, the action generated by transforming the message from the first format into a target specific payload based on the intent of the message and one or more software application interfaces operable by the one or more entities;
causing the action to be executed at the one or more software application interfaces operable by the one or more entities by processing the target specific payload at the healthcare management server in association with the user and the one or more entities; and
causing a result of the action to be presented to the user.

2. The method of claim 1, further comprising:
determining clinical data associated with the user;
determining a machine learning model to process the message based on the clinical data; and
determining a portion of the intent of the message based on the machine learning model.

3. The method of claim 1, wherein a classifier model of the one or more classifier models is trained based on a training data set of historical messages received through an engagement channel by the healthcare management server.

4. The method of claim 3, wherein the engagement channel comprises one of an email request, a web request, a mobile application, and a call center request.

5. The method of claim 1, wherein the one or more classifier models comprises a set of artificial intelligence or machine learning models.

6. The method of claim 5, wherein the set of artificial intelligence or machine learning models comprises at least one of a classifier deep learning model, a multi classifier deep learning model, a bidirectional Gated Recurrent Unit, a named entity recognition deep learning model, and a bidirectional Long Short Term Memory-Convolutional Neural Network.

7. The method of claim 1, wherein the one or more classifier models are trained through at least one of supervised learning, unsupervised learning, and semi-supervised learning.

8. The method of claim 1, wherein at least one of the one or more classifier models is accessed through one or more cognitive services.

9. The method of claim 1, wherein one metadata item about the message comprises a priority level.

10. The method of claim 1, wherein the message is received from the user associated with a particular region, the method further comprising:
    determining a list of intents and entities based on a training dataset of historical messages associated with the particular region,
    wherein the message classification job is processed using at least one classifier model trained on the training dataset of historical messages associated with the particular region.

11. A system comprising one or more processors and memory operably coupled with the one or more processors, wherein the memory stores instructions that, in response to execution of the instructions by one or more processors, cause the one or more processors to perform operations including:
    receiving, through an intelligent message handling application, a message in a first format of multiple possible formats from a user;
    determining, at a healthcare management server, a plurality of metadata items about the user and the message, the plurality of metadata items including at least a directed acyclic graph (DAG) describing one or more processing activities to be performed on the message, the plurality of metadata items further including a unique correlation identifier associated with the message based on the user;
    generating, at the healthcare management server, a message classification job based on the plurality of metadata items about the user and the message;
    processing the message classification job using one or more classifier models based on the DAG;
    determining an intent of the message and one or more entities based on the processing of the message classification job;
    generating an action pre-defined in the DAG to execute in association with the one or more entities based on the intent of the message and the unique correlation identifier, the action generated by transforming the message from the first format into a target specific payload based on the intent of the message and one or more software application interfaces operable by the one or more entities;
    causing the action to be executed at the one or more software application interfaces operable by the one or more entities by processing the target specific payload at the healthcare management server in association with the user and the one or more entities; and
    causing a result of the action to be presented to the user.

12. The system of claim 11, wherein the operations further comprise:
    determining clinical data associated with the user;
    determining a machine learning model to process the message based on the clinical data; and
    determining a portion of the intent of the message based on the machine learning model.

13. The system of claim 11, wherein a classifier model of the one or more classifier models is trained based on a training data set of historical messages received through an engagement channel by the healthcare management server.

14. The system of claim 13, wherein the engagement channel comprises one of an email request, a web request, a mobile application, and a call center request.

15. The system of claim 11, wherein the one or more classifier models comprises a set of artificial intelligence or machine learning models.

16. The system of claim 15, wherein the set of artificial intelligence or machine learning models comprises at least one of a classifier deep learning model, a multi classifier deep learning model, a bidirectional Gated Recurrent Unit, a named entity recognition deep learning model, and a bidirectional Long Short Term Memory-Convolutional Neural Network.

17. The system of claim 11, wherein the one or more classifier models are trained through at least one of supervised learning, unsupervised learning, and semi-supervised learning.

18. The system of claim 11, wherein at least one of the one or more classifier models is accessed through one or more cognitive services.

19. The system of claim 11, wherein one metadata item about the message comprises a priority level.

20. The system of claim 11, wherein the message is received from the user associated with a particular region and wherein the operations further comprise:
    determining a list of intents and entities based on a training dataset of historical messages associated with the particular region,
    wherein the message classification job is processed using at least one classifier model trained on the training dataset of historical messages associated with the particular region.

* * * * *